United States Patent
Gervais et al.

(10) Patent No.: US 11,808,704 B2
(45) Date of Patent: Nov. 7, 2023

(54) FLUORESCENCE-DETECTED ASSAYS ON MICROFLUIDIC CHIPS

(71) Applicant: ONE DROP DIAGNOSTICS SÀRL, Neuchâtel (CH)

(72) Inventors: Luc Gervais, Neuchâtel (CH); Jörg Ziegler, Grenchen (CH); Nicolas Descharmes, Renens (CH)

(73) Assignee: 1DROP SA, Neuchâfel (CH)

( * ) Notice: Subject to any disclaimer, the term of this patent is extended or adjusted under 35 U.S.C. 154(b) by 0 days.

(21) Appl. No.: 15/123,965

(22) PCT Filed: Mar. 5, 2015

(86) PCT No.: PCT/EP2015/054643
§ 371 (c)(1),
(2) Date: Sep. 6, 2016

(87) PCT Pub. No.: WO2015/132347
PCT Pub. Date: Sep. 11, 2015

(65) Prior Publication Data
US 2017/0016827 A1    Jan. 19, 2017

(30) Foreign Application Priority Data
Mar. 7, 2014  (EP) ..................... 14158334

(51) Int. Cl.
*G01N 21/64*    (2006.01)
*G01N 21/77*    (2006.01)
(Continued)

(52) U.S. Cl.
CPC ...... *G01N 21/648* (2013.01); *B01L 3/502715* (2013.01); *G01N 21/6428* (2013.01);
(Continued)

(58) Field of Classification Search
CPC ......... B01L 2300/0816; B01L 2200/16; B01L 2300/0864; B01L 2300/0867;
(Continued)

(56) References Cited

U.S. PATENT DOCUMENTS 5,344,784 A * 9/1994 Attridge ............. G01N 21/6428
385/12
6,137,117 A * 10/2000 Feldstein ........... G01N 21/6428
250/461.2
(Continued)

FOREIGN PATENT DOCUMENTS

EP    0 128 723 A2    12/1984
WO   WO 96/29589    9/1996
(Continued)

OTHER PUBLICATIONS

Schelb, M., et al., "Fluorescence excitation on monolithically integrated all-polymer chips," J of Biomedical Optics, 2010, July 7, vol. 15, No. 4, pp. 041517-1-041517-5.
(Continued)

*Primary Examiner* — Dean Kwak
(74) *Attorney, Agent, or Firm* — Pauley Erickson & Swanson

(57) ABSTRACT

An assay unit for carrying-out fluorescence-detected assays having a microfluidic chip with a microfluidic system to convey a sample or analyte solution through one or more microfluidic channels arranged on the chip, and a photonic system with two or more rectangular waveguide structures. The microfluidic channels and the waveguide structures cross each other at a detection site. In an assay area, where a certain microfluidic channel and a certain waveguide structure cross each other, one or more lateral surfaces of the core of the waveguide structure at least partially face an inner volume of the microfluidic channel, such that an evanescent field of light guided within the waveguide struc-
(Continued)

(51) Int. Cl.
   *B01L 3/00* (2006.01)
   *G01N 33/543* (2006.01)
(52) U.S. Cl.
   CPC ..... *G01N 21/7703* (2013.01); *G01N 21/7746* (2013.01); *G01N 33/54306* (2013.01); *B01L 2300/0627* (2013.01); *B01L 2300/0654* (2013.01); *B01L 2300/0816* (2013.01); *B01L 2300/0877* (2013.01); *B01L 2300/0887* (2013.01); *G01N 2021/6439* (2013.01); *G01N 2021/7736* (2013.01); *G01N 2021/7786* (2013.01); *G01N 2201/08* (2013.01)
(58) Field of Classification Search
   CPC .......... B01L 3/5027; B01L 2300/0627; B01L 2300/0654; B01L 2300/0877; B01L 2300/0887; B01L 3/502715; G01N 15/1484; G01N 2021/7736; G01N 2021/7786; G01N 21/6428; G01N 21/648; G01N 21/7703; G01N 21/7746; G01N 2201/08; G01N 33/54306
   USPC ... 422/82.05, 82.06, 82.07, 82.11, 502, 503; 385/4, 12, 14
   See application file for complete search history.

(56) References Cited

U.S. PATENT DOCUMENTS

| | | | |
|---|---|---|---|
| 6,192,168 B1 | 2/2001 | Feldstein et al. | |
| 6,198,869 B1 * | 3/2001 | Kraus | G01N 21/05 356/317 |
| 6,395,558 B1 | 5/2002 | Duveneck et al. | |
| 6,438,279 B1 | 8/2002 | Craighead et al. | |
| 7,175,811 B2 | 2/2007 | Bach et al. | |
| 7,410,784 B2 * | 8/2008 | Hatch | C12Q 1/001 435/174 |
| 7,564,045 B2 | 7/2009 | Ohman et al. | |
| 7,708,945 B1 * | 5/2010 | Abel | C12Q 1/6816 422/430 |
| 7,834,329 B2 | 11/2010 | Lundquist et al. | |
| 2002/0076154 A1 * | 6/2002 | Maisenhoelder | G01N 21/7743 385/37 |
| 2002/0110839 A1 | 8/2002 | Bach et al. | |
| 2004/0081384 A1 * | 4/2004 | Datesman | G01N 21/431 385/12 |
| 2006/0068490 A1 * | 3/2006 | Tang | B01F 5/0646 435/287.2 |
| 2007/0196043 A1 * | 8/2007 | Peled | G01N 21/7746 385/12 |
| 2007/0211254 A1 * | 9/2007 | Matsushita | G01N 21/553 356/445 |
| 2008/0152281 A1 | 6/2008 | Lundquist et al. | |
| 2009/0312188 A1 * | 12/2009 | Duer | B01L 3/502715 506/6 |
| 2009/0312200 A1 * | 12/2009 | Pompa | G01N 21/6456 506/39 |
| 2010/0041065 A1 * | 2/2010 | Horii | G01N 33/6857 435/7.1 |
| 2011/0012026 A1 | 1/2011 | Moll et al. | |
| 2012/0077190 A1 * | 3/2012 | Lundquist | G01N 21/6452 435/6.1 |
| 2013/0338013 A1 * | 12/2013 | Zhong | G01N 21/648 506/3 |
| 2014/0315760 A1 * | 10/2014 | Ratner | G01N 33/80 506/18 |

FOREIGN PATENT DOCUMENTS

| | | |
|---|---|---|
| WO | WO 98/09156 A1 | 3/1998 |
| WO | WO 2006/135306 A1 | 12/2006 |

OTHER PUBLICATIONS

Hofmann, O., et al., "Three-Dimensional Microfluidic Confinement for Efficient Sample Delivery to Biosensor Surfaces. Application to Immunoassays on Planar Optical Waveguides," Analytical Chemistry, Amer Chem Soc., 2002, Sep. 17, vol. 74, No. 20, pp. 5423-5250.
Ferris et al., "Evaluation of the Virus Counter® for Rapid baculovirus quantitation," National Institute of Health, vol. 171 (1), Jan. 2011, pp. 111-166.
Gervais and Delamarche, "Toward one-step point-of-care immunodiagnostics using capillary-driven microfluidics and PDMS substrates†+,"RSC Publishing, vol. 9, No. 23, Dec. 2009, pp. 3313-3452.
Gervais et al.,"Microfluidic Chips for Point-of-Care Immunodiagnostics, "Advanced Healthcare Materials, vol. 23, No. 24, Jun. 24, 2011, pp. 1-26.
Guirgis et al., "Gold nanoparticle-based fluorescence immunoassay for malaria antigen detection," Analytical & Bioanalytical Chemistry, vol. 402, No. 3, Nov. 17, 2011, pp. 1019-1027.
M.J. Levene et al., "Zero-Mode Waveguides for Single-Molecule Analysis at High Concentrations,"American Association for the Advancement of Science, vol. 299, Jan. 31, 2003, pp. 682-686.
Ligler et al., "Array biosensor for detection of toxins," Center for Bio/Molecular Science and Engineering, Naval Research Laboratory, vol. 377, Jun. 13, 2003, pp. 469-477.
Mogensen et al., "Integration of polymer waveguides for optical detection in microfabricated chemical analysis systems," © 2003 Optical Society of America, vol. 42, No. 19, Jul. 1, 2003, pp. 4072-4079.
A. Neyer et al., "Fabrication of Low Loss Polymer Waveguides Using Injection Moulding Technology,"Electronics Letters, vol. 29, No. 4, Feb. 18, 1993, pp. 399-401.
Okerman et al., "Simultaneous Determination of Different Antibiotic Residues in Bovine and in Porcine Kidneys by Solid-Phase Fluorescence Immunoassay," Journal of AOAC International, vol. 86, No. 2, 2003, pp. 236-240.
Shibata et al., "Injectable hydrogel microbeads for fluorescence-based in vivo continuous glucose monitoring," PNAS, vol. 107, No. 42, Oct. 19, 2010, pp. 17894-17898.
Sun et al., "Determination of 17-oestradiol by fluorescence immunoassay with streptavidin-conjugated quantum dots as label," Elsevier Steroids , vol. 75, Feb. 2, 2010, pp. 400-403.
Hofmann et al., "Three-Dimensional Microfluidic Confinement for Efficient Sample Delivery to Biosensor Surfaces. Applications to Immunoassays on Planner Optical Waveguides," © 2002 American Chemical Society, Analytical Chemistry, vol. 74, No. 20, Oct. 15, 2002, pp. 5243-5249.
Schelb et al., "Fluorescence excitation on monolithically integrated all-polymer chips," Journal of Biomedical Optics, vol. 15, No. 4, Jul./Aug. 2010, pp. 041517-1 to 041517-5.
Vannahme et al., "Plastic lab-on-a-chip for fluorescence excitation with integrated organic semiconductor lasers," © 2011 Optical Society of America, Optics Express, vol. 19, No. 9, Apr. 25, 2011, pp. 8179-8186.
Zhang et al., "An Indirect Competitive Fluorescence Immunoassay for Determination of Dicyclohexyl Phthalate in Water Samples," © Springer Science+Business Media, LLC 2010, Mar. 30, 2010, pp. 1167-1173.
Zoha et al., "Ultrasensitive Direct Fluorescent Immunoassay for Thyroid Stimulating Hormone,"*Clinical Chemistry*, Oak Ridge Conference, vol. 44, No. 9, 1998, pp. 2045-2046.

* cited by examiner

Fig. 5
(a)
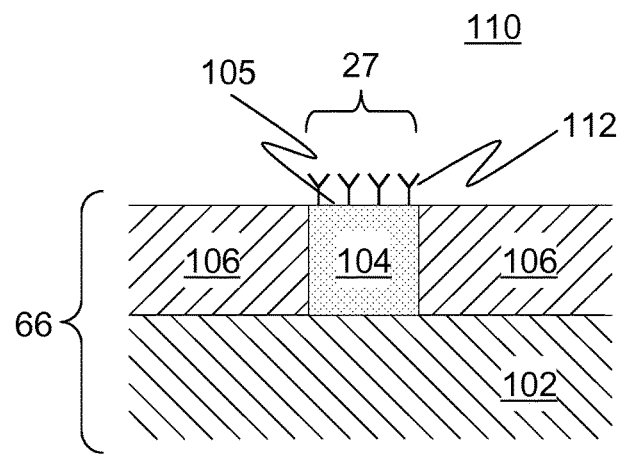
(b)
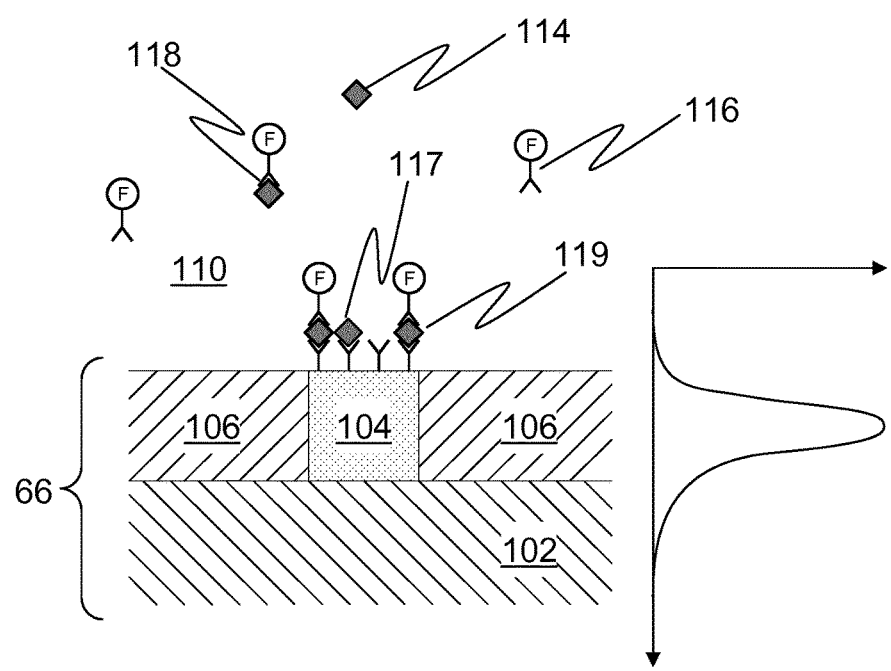

Fig. 8
(a)
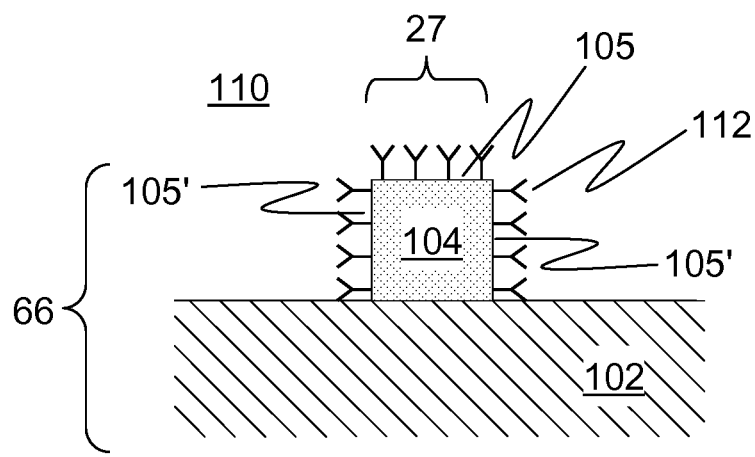
(b)
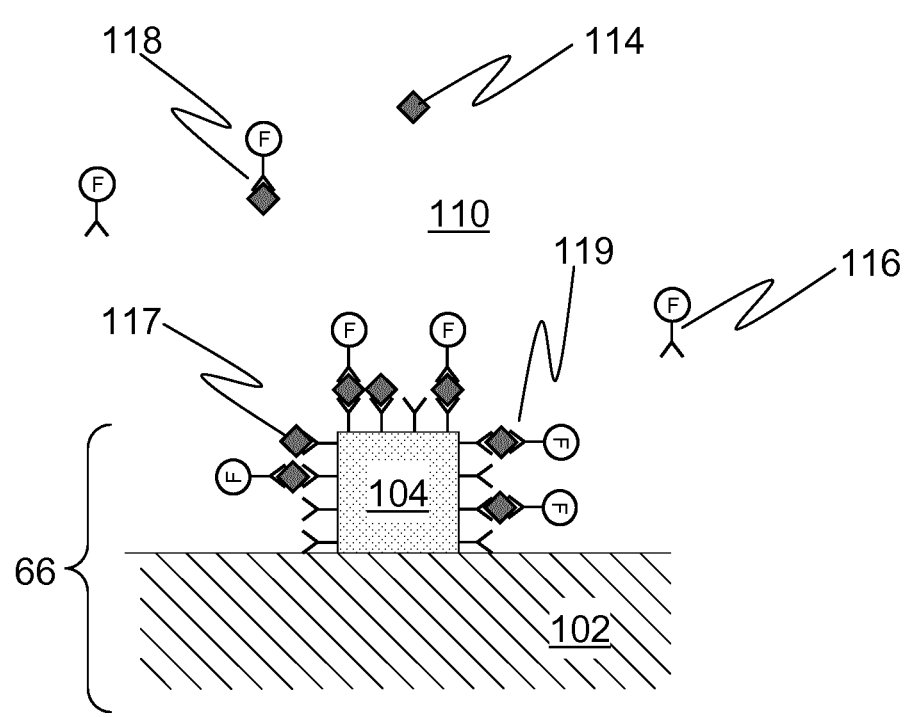

Fig. 9
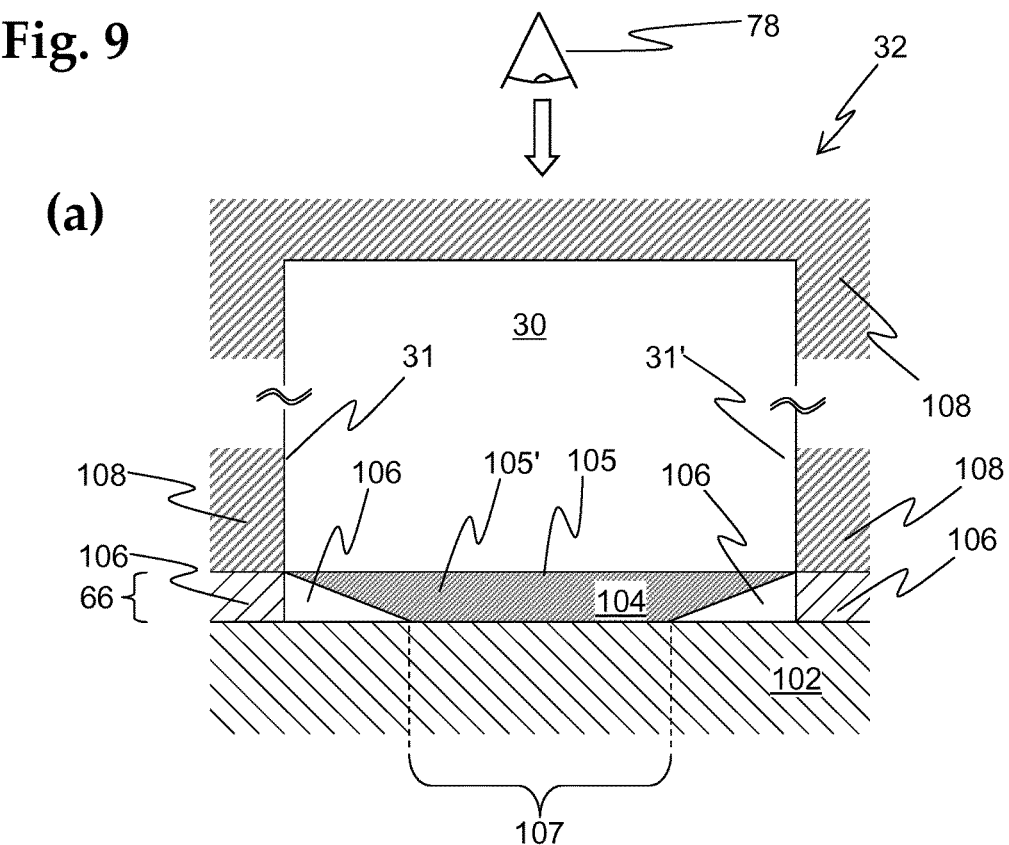
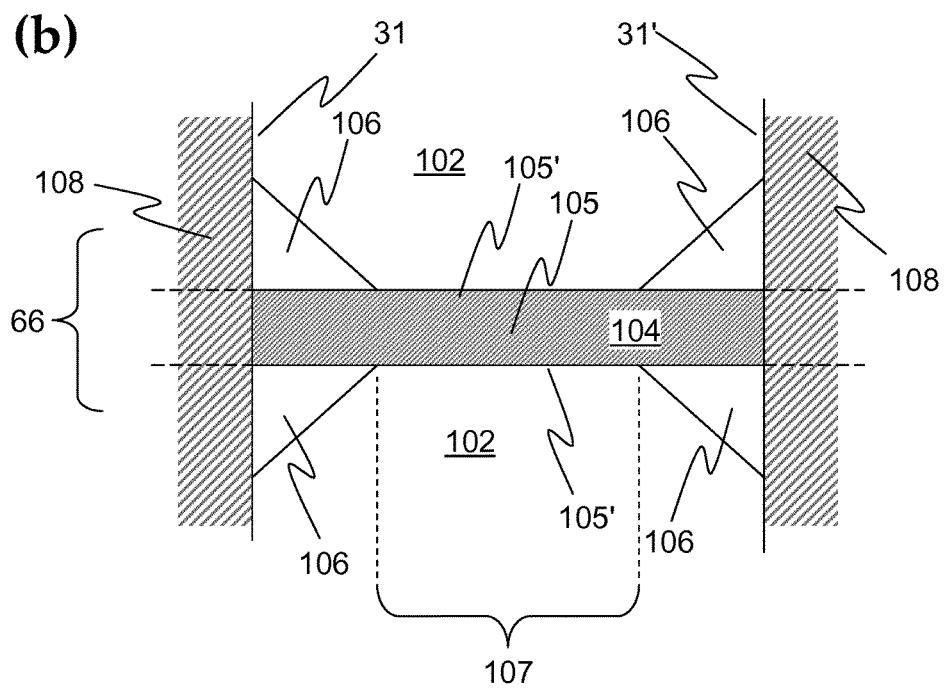

Fig. 13
(a)
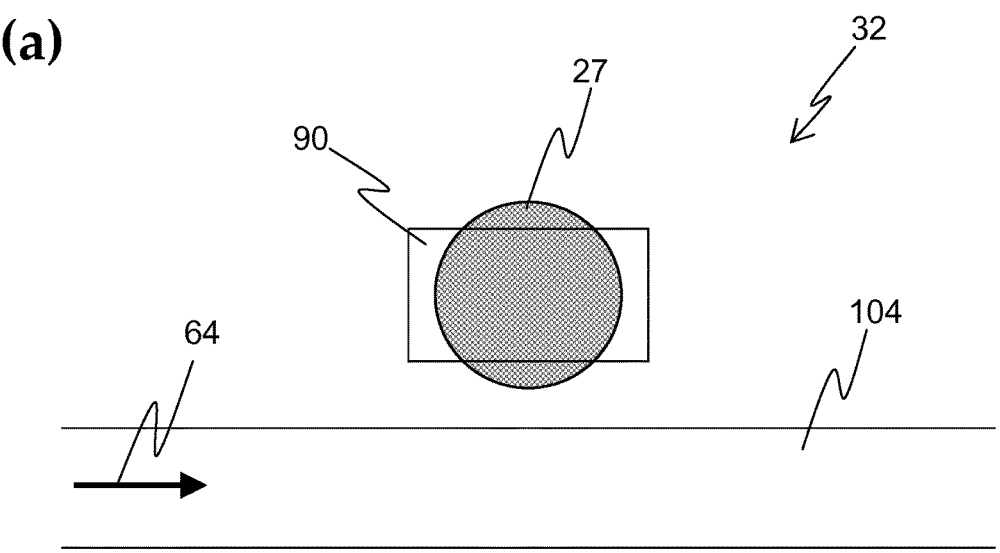
(b)
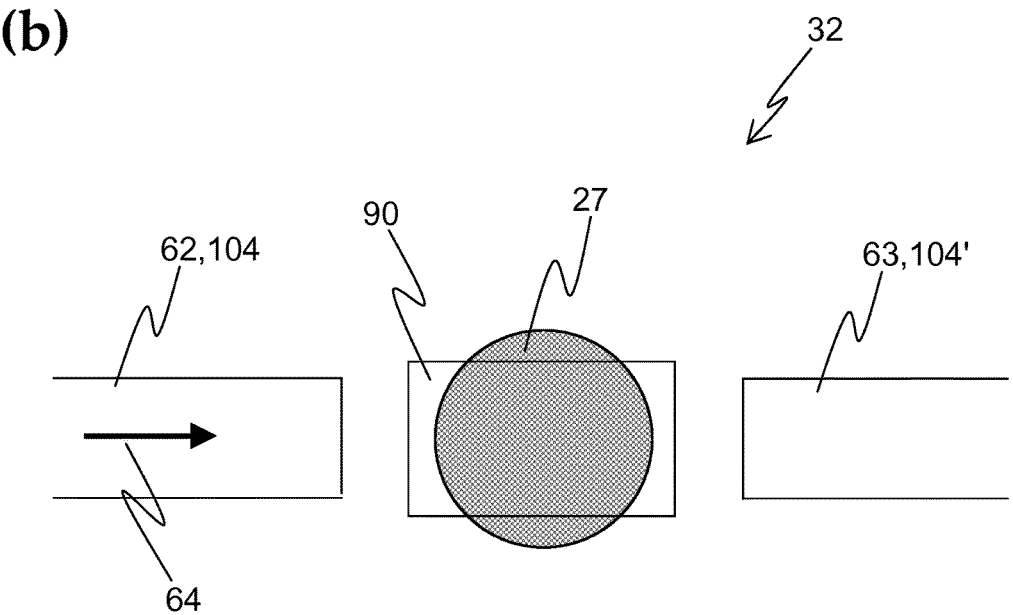

FLUORESCENCE-DETECTED ASSAYS ON MICROFLUIDIC CHIPS

BACKGROUND OF THE INVENTION

Field of the Invention

The invention relates to assay units for carrying out fluorescence-detected assays, reader units for reading the results of such assay units, and diagnostic devices with such assay units and reader units, according to the preamble of the independent claims.

Discussion of Related Art

Physiological samples such as for example body fluids may be analyzed for a wide variety of biochemical analytes. Accurate medical diagnostics is an important part of medical treatment such as the identification of health conditions and disease, monitoring, prognosis, and companion diagnostics. There are two main settings in which medical diagnostics systems are used: dedicated medical laboratories and the so-called point-of-care (PoC) testing.

The term "physiological sample" in the context of this description shall comprise all material that is either biological material obtained from the patient, such as blood, urine, stool, or tissue, or samples that are prepared for subsequent analysis based on such biological material.

Laboratory diagnostic devices as used in medical laboratories generally provide a wide variety of analytical capabilities. Laboratory diagnostic devices are sensitive, accurate and flexible, and provide a high throughput. However, they also have the disadvantage of being expensive, and requiring well trained personnel for operation. For this reason such diagnostic devices are mainly used in hospital laboratories and centralized medical laboratories, where they can be used most efficiently. However, since such devices require a physiological sample from a patient, said samples have to be transported to the medical laboratory, where the analysis is going to be performed, and have to be handled and stored appropriately. As a result, the results of the analysis are available only after hours or even days.

An increasingly large number of diagnostic tests are carried out at the point of care, close to the patient, for example in a medical practice, an emergency room of a hospital, an ambulance vehicle, at the patient's side, at home or in the field. Point-of-care diagnostic devices are often portable, and capable of obtaining analytical results rapidly (within minutes). Their use is generally much simpler, so that the diagnostic tests can be carried out by medical personnel without special training, or even by the patient himself. Devices used for point-of-care diagnostics analyse small sample volumes, are low cost and easy to use. Results can be obtained directly after the introduction of the sample onto the device. Point-of-care diagnostic tests provide a snapshot of the biochemical state of the body. In hospitals and clinics, they are used by medical practitioners as an alternative or as a complement to clinical laboratory analysers. They are also used outside of the hospital, at home or in the field.

Current point-of-care diagnostics devices are often not accurate or sensitive enough to be relied on as the only source of information. Diagnostics tests thus often need to be redone in a clinical laboratory. One challenge therefore is to develop point-of-care diagnostics devices that are sensitive and accurate enough to provide an equal alternative to clinical laboratories.

Recently, new generations of microfluidic chips for point-of-care diagnostics have been developed, as for example disclosed in the two following articles: L. Gervais, E. Delamarche, "*Toward One-step Point-of-care Immunodiagnostics Using Capillary-driven Microfluidics and PDMS Substrates*", Lab on a Chip 9, no. 23 (2009): 3330. doi:10.1039/b906523g; and L. Gervais, N. de Rooij, E. Delamarche, "*Microfluidic Chips for Point-of-Care Immunodiagnostics*", Advanced Materials 23, No. 24 (Jun. 24, 2011): H151-H176. doi:10.1002/adma.201100464.

After the simple addition of a drop of blood (less than 20 microliter), and using very low volumes of integrated reagents (a few picoliters), the microfluidic chips can perform highly sensitive (picomolar) and accurate (coefficient of variation lower than 10%) multiplexed detection of tens of different proteins. While these microfluidic chips are powerful, they are still expensive to manufacture in silicon, and they require an expensive high-end fluorescence microscope for optical signal acquisition and quantification.

Fluorescence is one of the main transduction techniques used for biochemical detection, and can be used for the detection of a variety of analytes, particularly viruses, proteins, nucleic acids, small molecules, and ions. A fluorescent molecule (fluorophore), being in a ground energy state, absorbs a photon at a certain excitation wavelength. After internal relaxation of the excited state to a lower energy level, a photon is spontaneously emitted, resulting in fluorescence radiation.

For analytical purposes, the measurable fluorescence emission has to be dependent on the presence of the analyte. There are two important approaches.

In one approach a suitably prepared fluorophore (a so called fluorescence marker) is bound to the analyte. After separation of analyte and unbound fluorophore, the amount of detected fluorescence radiation allows to determine the amount of analyte. In the typical case of an immunoassay, in a first step a fluorescence marker is selectively bound to protein analytes: A fluorescence marker is prepared by covalently binding a fluorophore to an antibody. The fluorophore antibody complex then binds specific to the protein analyte. In a second step, the specific analytes to be detected are selectively bound to corresponding antibodies that have been immobilized on a surface or a solid phase. As a result, the analytes that shall be detected are also immobilized on the solid phase, together with the fluorophore.

In particular, the surface fluorescence immunoassay is the workhorse of pharmaceutical and diagnostics companies. Microarray slides can contain hundreds of thousands of capture spots, and can be used to perform massively multiplexed protein and nucleic acid assays. Fluorescence detection is extremely sensitive and can detect single molecules on a surface with high accuracy. Such powerful laboratory based systems integrating protein and nucleic acid microarray slides and microarray optical readers are sold by manufacturers such as Agilent, Illumina, Affymetrix, bio-Rad, and Arrayit.

In another approach, used for the detection of small molecules and ions, the analyte interacts with a fluorophore, thereby influencing its fluorescent behaviour. By comparing the resulting fluorescence with the expected fluorescence in absence of the analyte, the amount of present analyte can be determined. For example may the analyte interact with the fluorophore in such a way that non-radiative relaxation pathways within the fluorophore are more preferred than radiative pathways, in which a photon is emitted, thereby reducing the resulting fluorescence radiation for a given excitation power (so called fluorescence quenching).

Analytes such as viruses and proteins can be detected following both methods. The device "Virus Counter 2100" from ViroCyt can be used for viral titering using fluorescent labels. Viruses are stained with two different fluorescent dyes, one specific for nucleic acids, and the other specific for a membrane protein of the virus. The virus counter then counts events where there are both fluorescent outputs. These events are counted and combined with the flow rate to determine the volumetric virus particle concentration. M. M. Ferris et al. ("*Evaluation of the Virus Counter for rapid baculovirus quantitation*", J. Virol. Methods, 171 (2011), 111) report that quantifying baculovirus samples above approx. 106 vp/mL using the Virus Counter 2100 results in viral detection that is as reliable as plaque assays, the current gold standard for viral titering.

In competitive fluorescence assays, unlabeled analyte from the sample competes with fluorescently labeled analyte added to the sample for antigen sites on the solid phase. B. Guirgis et al. ("Gold nanoparticle-based fluorescence immunoassay for malaria antigen detection", Anal. Bioanal. Chem. 402 (2002), 1019) developed a competitive fluorescence immunoassay to detect malaria antigens in blood samples.

Fluorescent labelling is also used in molecular diagnostics to detect specific sequences in DNA or RNA. For example, Randox sells a device called "FH-Array" to detect familial hypercholesterolemia, and cystic fibrosis can be detected on the MiSeqDx platform of Illumina.

Fluorescence immunoassays are also used to detect small molecules, such as hormones, antibiotic residues or phthalate esters. S. J. Zoha et al. (Clinical Chemistry 44 (1998), 2045) used a fluorescence immunoassay to detect the thyroid stimulating hormone TSH. M. Sun et al. (Steroids 75 (2010), 400) used a fluorescence immunoassay to detect estradiol. Indexx laboratories developed Parallux, a fluorescence immunoassay to detect antibiotic residues in milk. L. Okerman et al. (Journal of AOAC International, 86 (2003), 236) used the Parallux immunoassay to simultaneously detect different antibiotic residues in bovine and porcine kidneys. To determine dicyclohexyl phthalate in water, M. Zhang, Y. Sheng (J. Fluoresc. 20 (2010), 1167) developed a competitive fluorescence immunoassay to detect glucose. H. Shibata et al. (PNAS 107 (2010), 17894) synthesized a fluorescent monomer composed of a glucose-recognition site, a fluorogenic site, spacers, and polymerization sites. By observing the fluorescence intensity they could successfully trace the blood glucose concentration fluctuation in blood in a highly-sensitive range. The CDI BloodParameterMonitoring System from Terumo Cardiovascular is capable to detect blood gases such as pH, $pCO_2$, $pO_2$, $K^+$, oxygen saturation ($sO_2$), etc. using their fluorescence detection technology.

Despite their many benefits, high-sensitivity fluorescence detection systems also have several limitations. A large optical reader system is usually needed, with a large and complex optical train, typically employing confocal laser scanning microscopy. Additionally, many of the described systems have very limited fluidic control, requiring trained personnel for pipetting, or pipetting robots, or active pumping. Furthermore, biochemical reactions on surfaces and in large reaction vessels, have large diffusion distances, causing them to operate in a transport-limited regime. These combined limitations mean that highly sensitive fluorescence detection is uncommon in point-of-care diagnostics.

One of the key remaining challenges is the miniaturization of the instrumentation for signal readout without a decrease in performance. The equivalent of a high-end optical microscope needs to be miniaturized to a handheld device.

One approach is to integrate fluidic, optical and biochemical structures directly on the chip. The proximity of the functional elements, and the miniature distances (compared to laboratory equipment), allow for much more efficient use of power while maintaining high performance.

One critical aspect for a successful assay is the signal to noise ratio (S/N). In the specific frame of this disclosure, this corresponds to the amount of signal that is recorded in the presence of fluorescently emitted light, over the amount of signal recorded by the same sensor in the absence of fluorescence. A system displaying a large S/N is able to distinguish with higher certainty positive detection events over negative ones. A large S/N is also necessary in order to enable the quantification of the detected analyte. In this case, the minimum concentration that can be detected, that is, the detection limit, is a function of the signal to noise ratio. Similarly, the sensitivity of the assay, that is, the minimum difference between two concentrations that the assay is capable of distinguishing, directly depends on the S/N.

In a standard fluorescence assay, the excitation light is provided using a free propagating beam and exposes a large area. This method suffers three main drawbacks. First of all, the excitation beam usually covers a much larger region than one or several detection sites. This is necessary to ensure good uniformity of the excitation across the chip for example. As a consequence a large fraction of the excitation power usually remains unused, thus artificially decreasing the local power density of excitation for the fluorophores or, its corollary, increasing the total amount of excitation power required. Second, the light that is not absorbed by the fluorophores is still free to propagate within the detection system. This generates a large amount of unwanted light that decreases the overall signal to noise ratio. The use of very high quality filters might become necessary to achieve acceptable S/N, thus increasing the total cost of the system. Third, the existence of excitation light outside of the detection regions can be detrimental to the S/N through the generation of parasitic fluorescence emission. This parasitic fluorescence can be emitted either by the material composing the chip, often referred to as autofluorescence, or from other compounds in the sample to be tested. The later is very common in the case of fluorescence assays in physiological samples such as whole blood or plasma.

In the case of a fluorescence-detected immunoassay, a successful assay relies on the capacity to efficiently discriminate between regions of high fluorescence marker density and regions of low fluorescence marker density. This capacity requires: (i) an efficient excitation of the fluorescence markers, (ii) a thorough separation of the excitation light from the weaker fluorescence emission signal, (iii) a sharp segregation of the bound markers from the free, unbound ones, and finally (iv) a sensitive detection of the fluorescence emission of the fluorescence markers.

Evanescent wave excitation has been used as an approach to tackle said requirements, which has led to the development of a variety of detection systems. Evanescent waves can be generated in strongly light-confining structures such as waveguides and cavities, and allow to selectively excite the fluorescent markers in the vicinity of a surface of such structures. In the following, the physical principles of evanescent waves in waveguide structures will be explained in more detail.

A waveguide is a structure that confines light and imposes that it propagates in either one or two dimensions only. In the scope of planar integrated optics, two types of waveguides can be distinguished: slab waveguides (one-dimensional) and rectangular waveguides (two-dimensional).

A slab waveguide consists of a layer of high refractive index material positioned in-between two layers of lower refractive index materials. Light that is injected in the higher refractive index layer can freely propagate within the plane defined by the layer but not outside (confinement in one dimension). In this configuration the intensity of a guided wave that results from the injection of a focused beam decreases quadratically as the distance between the injection point and the measurement point increases.

A rectangular waveguide consists of a linear structure with a rectangular cross section with a high refractive index that is surrounded on the four sides with one or several media of lower refractive indices. In this configuration, light injected in the waveguide structure can freely propagate along the high refractive index region, but is prevented from escaping towards the lower refractive index media on the sides. This corresponds to a two dimensional confinement. This type of structure can easily propagate light without significant variations of the light intensity over extended distances.

The existence of an evanescent wave near a strongly confined guided wave can be understood by considering the example of a planar waveguide. Following Maxwell equations, a propagating electromagnetic wave that verifies the vectorial Helmholtz equation, can be written for the electric field component as:

$$\nabla^2 E(r) + k^2 E(r) = 0$$

Here E(r) refers to the vectorial electric field and k is the propagation wave vector. The same equation could be written for the associated magnetic field H(r). Each component of the vectorial fields ($E_x$, $E_y$, $E_z$, $H_x$, $H_y$, $H_z$) must therefore verify the scalar Helmholtz equation, where $\psi(r)$ is any of the above field components.

$$\nabla^2 \psi(r) + k^2 \psi(r) = 0$$

Let us consider the most general case of an asymmetric waveguide. It is composed of three layers of distinct refractive indices: a substrate layer (lower layer), a core layer (intermediate layer) with the highest refractive index, and a cladding layer (upper layer). In the case of an assay device, the cladding layer could be a physiological medium such as saliva, urine, blood or plasma, having a refractive index n between 1.33 and 1.36 in the visible range. In comparison, the core and cladding layer can be made out of glass (refractive index n typically between 1.45 and 1.9 in the visible), semiconductors such as silicon nitride (n approx. 2), or gallium-nitride (n approx. 2.38), or more advantageously polymers such as Polymethylmethacrylate, Polycarbonate, or Polystyrene. The refractive index n of said polymers can be typically of the order of 1.45 to 1.6.

Note that all the materials and refractive index values mentioned earlier are given for operation in the visible range of the spectrum. It should also be noted that the test medium could also display absorption at certain wavelengths, which can be modelled in the form of a complex refractive index n=η+iκ with κ≠0.

Two examples of optical devices including polymer-based waveguides are disclosed in the following two articles: A. Neyer, T. Knoche, L. Müller, "*Fabrication of Low Loss Polymer Waveguides Using Injection Moulding Technology*", Electronics Letters 29, no. 4 (1993): 399-401, and K. B. Mogensen, J. El-Ali, A. Wolff, J. P. Kutter, "*Integration of Polymer Waveguides for Optical Detection in Microfabricated Chemical Analysis Systems*", Applied Optics 42, no. 19 (2003): 4072-4079.

Independently of the choice of material, the optical problem consists of finding an electric (respectively magnetic) field distribution that verifies the scalar Helmoltz equation in each of the three layers. It is common to simplify the problem by decomposing the set of electromagnetic waves on the basis of two polarizations, namely transverse electric (TE) and transverse magnetic (TM). Considering only the case of a TE wave that propagates along z in a layered medium, where x is the direction of the stack and y is considered infinitely invariant, the problem can be rewritten as:

$$\frac{\partial^2}{\partial x^2} E_y(x) + \left(k_0^2 n^2(x) - \beta^2\right) E_y(x) = 0$$

for the following refractive index profile:

$$\begin{cases} n(x) = n_{clad} & d \leq x \\ n(x) = n_{core} & 0 \leq x \leq d \\ n(x) = n_{sub} & x \leq 0 \end{cases}$$

with β being the propagation wave number along the guide direction, and d being the thickness of the core layer.

The previous equation can thus be rewritten in the form of a system of equation, each of which is valid within the considered layer, and verifying continuity relationships for $E_y(x)$ and its second derivative at each interface. The system of equation can be written as:

$$\begin{cases} \frac{\partial^2}{\partial x^2} E_y(x) - \kappa_{clad}^2 E_y(x) = 0 \\ \frac{\partial^2}{\partial x^2} E_y(x) + \alpha^2 E_y(x) = 0 \\ \frac{\partial^2}{\partial x^2} E_y(x) - \kappa_{sub}^2 E_y(x) = 0 \end{cases}$$

where:

$$\begin{cases} -\kappa_{clad}^2 = n_{clad}^2 k_0^2 - \beta^2 \\ \alpha^2 = n_{core}^2 k_0^2 - \beta^2 \\ -\kappa_{sub}^2 = n_{sub}^2 k_0^2 - \beta^2 \end{cases}$$

The system of equation can have either odd or even solutions. Considering only the even case, like in the case of the fundamental mode, the solution would be:

$$\begin{cases} E_y(x) = E_{clad} e^{-\kappa_{clad}^2 (d-x)} \\ E_y(x) = E_{core} \cos(\alpha x - \phi_s) \\ E_y(x) = E_{sub} e^{-\kappa_{sub}^2 x} \end{cases}$$

with $\Phi_S$ being the phase shift. It can be seen above that a part of the electric field of the guided mode spatially extends into the substrate and the cladding with decay constants $\kappa_{clad}^2$ and $\kappa_{sub}^2$ respectively. These two exponentially decaying tails are referred to as the evanescent tails of the guided mode, and can be used for example to excite absorbing molecules such as fluorophores located near the interface. The decay constants depend mainly on the relative refractive indices and the degree of asymmetry of the waveguide, as well as on the excitation wavelength.

In the existing systems using evanescent waves for exciting fluorophores, the evanescent wave is generated by total internal reflection of an incident wave on an interface of a light guiding structure.

Light guiding structures are generally distinguished according to whether they are based on optical fibres, or whether they are planar. In the same manner, evanescent wave excitation structures have been developed based on either optical fibres or planar structures.

The systems as described in WO 96/29589 A1 and EP 0128723 A2 for example correspond to optical fibre based or optical fibre-like structures for immunoassays. The outer surface of an optical rod or fibre is coated with biochemical capture molecules. The solution to be tested is then brought into contact with this functionalized surface. Target and capture molecules bind to each other through a biochemical reaction. The creation of a guided wave within the structure allows for the local excitation of the fluorescently labelled target-capture complex located in the immediate vicinity of the surface. Fluorescently labelled target molecules and unbound fluorescent labels that are located further away within the solution are not excited and thus, do not generate a parasitic background emission. In the same way, only fluorescently labelled target-capture complexes located on the surface are capable of coupling fluorescent light back into the guiding structure. The latter can then be isolated from the excitation light by means of an optical filter, and is measured using a photodetector.

The use of planar structures for the evanescent excitation of fluorescence in assays has also received a lot of attention. These structures usually comprise of one or more thin layers of higher refractive index, deposited on top of one or more substrate layers of lower refractive indices. While the thickness of the guiding layer is comparable with the excitation wavelength, the lateral dimensions of the layer are usually much larger.

The higher degree of integration and the easier fabrication and assembly processes are strong benefits of planar devices over optical fibres. A variety of systems have been developed based on this principle. In U.S. Pat. No. 5,344,784, a structure comprising a transparent dielectric substrate, a buffer layer with a refractive index that is less than the substrate, and a waveguide layer in the form of a thin dielectric film deposited on the buffer layer. Said waveguide layer has a refractive index that is higher than the substrate. A layer of reagent is then deposited on top of the waveguiding layer, facing the liquid to be tested. An excitation light beam with a suitable wavelength passes from the back through the transparent substrate and impinges on the interface between substrate and buffer layer with a certain angle that is chosen such that the exciting radiation is totally internally reflected, and the evanescent field penetrates the buffer layer. As a consequence of evanescent coupling, excitation radiation is propagated within the high-refractive-index waveguide layer. The binding of fluorescently labelled molecules or particles onto the surface is then revealed through the evanescent excitation of the markers. The fluorophores bound to the surface are excited by the evanescent field, and emit fluorescence radiation. A part of the fluorescence emission couples back through the system, and produces a narrow cone of fluorescence light that leaves the substrate layer on the back side, where it is detected.

WO 2006/135306 A1 discloses a similar system, which in addition comprises a pattern of microstructures located above the waveguiding layer.

In US 2011/012026 A1, a combination of two facing waveguide layers separated by a gasket is used. The solution to be tested is introduced between the two guiding layers, thus effectively increasing the interaction area.

Another approach uses two-dimensional waveguides to direct the excitation wave towards a micrometer scale or submicron scale structure that serves as a confinement region for the analyte. In this case, the guiding structure has dimensions comparable with the excitation wavelength both vertically and horizontally. One effect of this configuration is that the excitation light does not need to be brought into the system near the reaction site, but can be coupled within the structure at a certain distance and then guided with little attenuation towards the reaction region.

US 2002/110839 A1 describes a system in which small wells are integrated in the upper cladding of a set of two-dimensional waveguides. The upper cladding is made out of a dielectric material. The bottom of the well, where the analyte is located, is in contact with the evanescent tail of the guided mode and thus the fluorescent markers bound to the waveguide core can be excited.

In the detection system described in US 2008/152281 A1, a similar approach is taken. One or several wells are fabricated in a mask layer. The bottom of each of these wells is in contact with the core of one or several waveguides.

Another efficient implementation of such a system can be found in the following article: M. J. Levene, "*Zero-Mode Waveguides for Single-Molecule Analysis at High Concentrations*", Science 299, no. 5607 (Jan. 31, 2003): 682-686. In this work, sub-wavelength apertures are created in a metallic layer, forming zero-mode waveguides of the metal-clad structure. This configuration allows enhancement of the fluorescent emission and imaging of low fluorescent light levels down to one single fluorophore.

In yet another approach, a set of excitation waveguides can be used in conjunction with a set of microfluidic channels in order to perform assays. A demonstration of such a system can be found in the following article: F. S. Ligler, Ch. Rowe Taitt, L. C. Shriver-Lake, K. E. Sapsford, Y. Shubin, J. P. Golden, "*Array Biosensor for Detection of Toxins*", Analytical and Bioanalytical Chemistry 377, no. 3 (Oct. 1, 2003): 469-477. Compared to the above-mentioned micro well approach, such a system has the advantage of a simpler fabrication and implementation, making the approach attractive in the prospect of a disposable device. This approach also presents clear advantages in terms of kinetics of the biochemical reactions. Nevertheless, such a system does also suffer from two main drawbacks. First of all, the absence of appropriate filtering functions in the microfluidic device imposes the use of pre-processed biological fluids, thus excluding the use of the device outside of the laboratory. Second, the microfluidic layers need to be pealed before rinsing and imaging the fluorescent spots. These operations are prohibitive to applying this method in a point-of-care device.

In the article "*Plastic lab-on-a-chip for fluorescence excitation with integrated organic semiconductor lasers*" (Ch. Vannahme et al., Optics Express 8179, 2011), a lab-on-chip platform for the realization of fluorescence-based assays from is disclosed. The microfluidic chip is made of Polymethylmethacrylate (PMMA), and comprises a microfluidic channel to carry the fluid to be analysed, and a set of waveguides crossing the microfluidic channels. Integrated organic semiconductor lasers for generation of the excitation radiation are realized as optical gain regions obtained from the deposition of an organic semiconductor (Alq3) doped with an organic dye (DCM) onto distributed Bragg gratings (DBG) to create lasing conditions. The lasers are pumped externally, and the emitted excitation light couples to the waveguides. The light is guided to an interaction zone at the intersection of waveguide and microfluidic channel, where it excites the fluorescence of an analyte suspended or in solution. The resulting fluorescence emission signal is detected with a CCD camera and a spectrometer.

In the disclosed microfluidic chip, the high degree of photonic integration (secondary laser source, grating and waveguides) creates a high level of complexity in the chip fabrication that is not favourable for the use of such microfluidic chips in a practical point-of-care scenario. First the in-print of DBG in PMMA is a rather fault intolerant process that is complicated to perform consistently in large series. Second, two high precision alignment steps are required for the creation of the photonic circuit. One step consists of the deep-UV exposure of PMMA for patterning the waveguides in alignment with the DBGs. The other step is the local deposition of the organic semiconductor and dye on the DBGs through mask obscuration. Finally, the consistency of inter-waveguides measurements is likely to be very dependent on the characteristics of each of the independent integrated lasers on the chip. Since the later display high sensitivity to fabrication, environment and operation conditions, low measurement accuracy has to be expected.

In the article "*Fluorescence excitation on monolithically integrated all-polymer chips*" (M. Scheib et al., J. Biomed. Optics 15(4), 041517, 2010) another lab-on-chip system is disclosed, where a PMMA substrate is etched and patterned in order to create a combination of a microfluidic channel and one or several waveguides that intersect perpendicularly. A variety of fluorescently labelled species (phospholipids and cells) are deposited at the intersection of the microfluidic channel and the waveguide. Excitation light is coupled into the planar waveguide by a glass fibre. At the intersection of channel and waveguide, the excitation light is coupled out of the end-facet of the waveguide, facing the channel side wall, where it excites immobilized fluorescent labels. Fluorescent light is then detected with an optical microscope.

In the disclosed system the coupling of excitation light is achieved through an optical fibre that is glued on an end facet of the waveguide. This rules out the possibility of using such a system in a disposable chip based point-of-care scenario. In addition, mode coupling between a circular optical fibre and a rectangular waveguide, though possible, requires great care in the design in order to be efficient. No information on this aspect is presented in the document.

A second major drawback comes from the disruption of the waveguide by the microfluidic channel. The guided light is forced to exit the waveguide and propagate in free space. In these conditions a significant amount of excitation light is expected to emerge from the sidewalls of the microfluidic chip and then be collected by the final imaging system, which considerably decreases the signal-to-noise ratio due to parasitic scattering.

U.S. Pat. No. 6,438,279 B1 discloses an assay chip setup with a ridge waveguide structure and a microfluidic channel, and a method to fabricate such devices. Excitation light is guided in a first waveguide to a microfluidic channel, where it leaves the waveguide structure and enters into the microfluidic channel, where it essentially illuminates a sample present in an interaction volume of a width of 1 µm or smaller and a depth between 0.125 and 1 µm, thereby exciting fluorophores present in said volume. After passing the interaction volume, excitation light is recollected using a second waveguide, which is distinct from the first waveguide, located opposite to the first waveguide that has been used to illuminate the sample volume. Emitted fluorescence light is detected by an external optical detection system.

Since the first waveguide ends at the interaction volume, excitation light is lost, due to diffraction and reflection at interfaces, and scattering in the sample volume for example. An enlarged width of the second waveguide is needed to efficiently collect and recouple as much light as possible. As a result the amount of excitation light present in the second waveguide after the microfluidic channel is considerably reduced. Since the loss of light is also caused by scattering of the light in the heterogeneous sample liquid, the resulting attenuation effect of the microfluidic channel is not reproducible, which renders the remaining excitation light essentially useless for further quantitative measurements.

The dimensions and materials needed for the disclosed system are unsuited for current mass fabrication methods in plastics such as injection moulding. Photolithography and reactive ion etching techniques are needed typically with Silicon, Silicon-dioxide and photoresist materials. Furthermore, interaction volumes with a width of 1 µm and below and a depth of 0.125 µm up to 1 µm are small compared to cellular components in whole blood, a typical analyte matrix for the described device. With whole blood as sample however there is a high chance to clog the interaction volume, since whole blood filtering cannot always remove all cellular components. In addition, channels with such small dimensions have a high resistance to fluidic samples. Implementing the described method into passive microfluidic systems is very difficult. Thus in the disclosed system fluids are conveyed electrophoretically.

In the article "*Three-dimensional Microfluidic Confinement for Efficient Sample Delivery to Biosensor Surfaces—Application to Immunoassays on Planar Optical Waveguides*" (O. Hofmann et al., Anal. Chem. 74, 5243, 2002), an experimental apparatus is disclosed, which allows for the investigation of the impact of a confinement flow on the rapidity at which a fluorescence-based immunoassay can occur. The experimental device comprises of a semiconductor waveguiding layer made out of silicon nitride (SiN) and silicon oxyde (SiO2), and a polydimethylsiloxane (PDMS) microfluidic flow cell arranged on top of the optical waveguide. The flow cell possesses two inlets, one for the injection of the solution to be analysed and the second one for the injection of a solution that allows for the tailoring of the interaction cross section of the analyte with the immunoreaction region. Excitation and detection of the fluorescence is performed via the planar waveguiding layer, wherein the evanescent part of the guided excitation light is used to excite immobilized fluorophores. The excitation light is coupled-in by means of a grating, and the same grating is used for the coupling-out of the fluorescence emission. A point detector is used to record the fluorescence signal.

The disclosed setup suffers from a number of disadvantages. First, the use of a slab waveguide/one-dimensional guiding layer has a negative effect on the overall excitation efficiency, which can be inferior by orders of magnitude, due to the lack of lateral confinement. Thus the disclosed setup can be expected to be unsuitable and not being properly functioning for longer distances between excitation light entry and assay site, particularly because also detection takes place via the slab waveguide, further decreasing the available light signal.

Second, the use of materials such as SiN and SiO2 is prohibitive for the realization of inexpensive disposable devices. Third, the measurement scheme disclosed measures the fluorescence emission that couples in and out of the waveguiding layer. This approach is not only very inefficient with respect to the total amount of fluorescence light emitted, it does not provide any spatial discrimination. This approach might therefore suffer from unwanted signal emanating from regions outside of the reaction region. It also prohibits the use of such a system for multiplexed applications, since any distinct assay area would couple its fluorescence signal into the same waveguide layer, without the possibility to distinguish certain signal parts from each other.

It should be emphasized that the detection methods described so far must be distinguished from those using similar types of planar guiding structures, where the detection scheme is based on a change of the local effective refractive index. An example of such a system is disclosed in U.S. Pat. No. 6,395,558 B1.

SUMMARY OF THE INVENTION

It is the overall objective of the present invention to provide an assay unit, and a diagnostic device with such an assay unit, that improve the state of the art with respect to the above-mentioned problems and other problems.

Particularly an assay unit and a diagnostic device according to the invention should allow carrying out fluorescence-detected assay tests with high sensitivity and precision, and an efficient use of excitation power.

An assay unit and a diagnostic device according to the invention should provide an enhanced signal-to-noise ratio, compared to transmission or reflection based fluorescence detection systems.

An assay unit and a diagnostic device according to the invention should provide a uniform evanescent wave excitation field to a variety of probes/assay areas distributed over an extended region.

The fluorescence signal of different assay areas should be unambiguously distinguishable.

The results of the assay should be accessible using a optical detection system of lower complexity than in the state of the art.

An assay unit according to the invention should advantageously be producible at low costs, with as few manufacturing steps as possible.

All elements of a diagnostic system according to the invention that come into contact with physiological sample or are contaminated in another way after use should advantageously be part of the assay unit, which generally will be disposed after use.

Advantageously, an assay unit according to the invention should be able to process physiological fluids without prior treatment.

These and other objects are substantially achieved by an assay unit, a reader unit, and a diagnostic device according to the independent claims. Further advantageous embodiments follow from the dependent claims and the description.

The present invention may comprise one or more of the features recited in the attached claims, and/or one or more of the following features and combinations thereof.

An assay unit according to the invention, for carrying-out fluorescence-detected assays on one or more physiological samples comprises a microfluidic chip with a microfluidic system that is able to convey a physiological sample or analyte solution through one or more microfluidic channels arranged on the chip, and a photonic system with two or more rectangular waveguide structures arranged on the chip that are able to guide excitation light in the near IR, visible, or near UV range. The one or more microfluidic channels and the two or more waveguide structures cross each other at a detection site. In an assay area, where a certain microfluidic channel and a certain waveguide structure cross each other, one or more lateral surfaces of the core of the waveguide structure at least partially face the inner volume of the microfluidic channel, such that an evanescent field of light guided within the waveguide structure overlaps with a certain part of the inner volume of the microfluidic channel.

In the context of this invention, a rectangular waveguide structure/two-dimensional waveguide is intended to include any essentially linear structure with an essentially rectangular cross-section with a certain refractive index that is surrounded by media of lower refractive indices, such that light coupled into the waveguide structure can freely propagate along the linear structure dimension, but is confined in the other two dimensions. This includes e.g. also linear waveguide structures with trapezoidal cross-section.

Using the evanescent field allows to excite the fluorophores present in the overlapping region of the microfluidic channel without considerably losing excitation light power in the waveguide, as it would be the case if the excitation light would cross the microfluidic channel. Thus it becomes possible to subsequently providing more than one microfluidic channel with an essentially uniform excitation light field, with only one waveguide structure, without losses due to scattering in the sample volume, or reflections etc. at interfaces.

In an advantageous embodiment of an assay unit according to the invention, one or more capture spots are located on the surface of the waveguide core, the capture spots comprising a coating of capture molecules of an assay, immobilized on said core surface.

For example may the capture spots comprise capture antibodies of an immunoassay.

The integration of both the microfluidic system as well as the photonic system necessary for exciting the fluorophores of an assay test on one chip, which can be called a "optofluidic chip", allow to produce such an assay unit cost efficiently, with known techniques used for producing microstructures on chips. The resulting assay unit, which has to be disposed after use, comprises only inexpensive parts.

In one advantageous embodiment of such an assay unit according to the invention, in an assay area the core layer of the waveguide structure is arranged on a substrate layer, and is embedded in a cladding layer, such that only an upper surface of the core opposite to the substrate layer faces the inner volume of the microfluidic channel.

In another advantageous embodiment of such an assay unit according to the invention, in an assay area the core layer of the waveguide structure is arranged on a substrate layer, and is at least partially not embedded in a cladding layer, such that both an upper surface of the core opposite to the substrate layer, and the two lateral surfaces face the inner volume of the microfluidic channel.

Advantageously, a waveguide structure comprises either a single waveguide, or a bundle of waveguides, said waveguides being either single mode waveguides, or multimode waveguides.

Advantageously, the assay unit according to the invention has one or more coupling elements for coupling a light beam into the one or more waveguides, and/or or more coupling elements for coupling a light beam out of the one or more waveguides.

A reader unit according to the invention, for reading out the results of an immunoassay carried out on an assay unit according to the invention as discussed above, comprises holder for releasably mounting an assay unit, one or more light sources for generating an excitation light beam, and a detector unit that is capable of measuring fluorescence emission light emitted by an assay unit mounted on the holder.

In an advantageous embodiment of such a reader unit, the detector unit is capable of obtaining a two-dimensional digital image of the fluorescence emission light of an assay unit mounted on the holder.

In a reader unit according to the invention, the detector unit advantageously comprises a digital image detector chip, for example a CCD chip.

A particularly advantageous embodiment of a reader unit according to the invention comprises optical elements for directing the excitation light beam toward coupling elements of an assay unit mounted on the holder.

A reader unit according to the invention can comprise a detection element for measuring the amplitude of excitation light coupled out from a waveguide of an assay unit mounted on the holder.

Such a feature has for example the advantage that fluorescence signals of assay areas excited by different waveguide structures can be quantitatively compared, or effects of the manufacturing process on the attenuation characteristics of different waveguide structures can be corrected, respectively.

A diagnostic device according to the invention, for carrying-out fluorescence-detected assay, comprises one or more assay units according to the invention as discussed above, and a reader unit according to the invention as discussed above.

BRIEF DESCRIPTION OF THE DRAWINGS

In order to facilitate a fuller understanding of the present invention, reference is now made to the appended drawings. These references should not be construed as limiting the present invention, but are intended to be exemplary only.

FIG. 5 schematically shows a cross-section through a possible geometry of a waveguide structure at a capture spot, along the axis of a microfluidic channel, (a) without analyte solution having passed the capture spot, and (b) with analyte solution present at the capture spot, and the electric field amplitude shown.

FIG. 8 schematically shows a cross-section through another possible geometry of a waveguide structure at a capture spot, along the axis of a microfluidic channel, (a) without analyte solution having passed the capture spot, and (b) with analyte solution present at the capture spot.

FIG. 9 schematically shows a waveguide core at a capture spot in a protruding geometry, (a) in a side view; and (b) in a top view.

FIG. 13 is a schematic view of two advantageous architectures for the excitation of an optical cavity using a waveguide.

DETAILED DESCRIPTION OF THE INVENTION

The examples provided hereinafter serve an improved illustration of the present invention, but are not suited for restricting the invention to the features disclosed herein. Components that are identical, or that are identical at least in terms of their function, are designated below by identical or at least comparable reference numbers.

The invention will be described using the fluorescence-detected immunoassay as an example for an fluorescence-detected assay test. However, as it is clear for a person skilled in the art, the invention can be realized with any other fluorescence-detected assay technique where fluorophores are permanently, or at some stage of the analytical process, immobilized on a surface. Thus the described embodiments of fluorescence-detected immunoassays on microfluidic chips shall represent only an illustrative example, and are not intended to restrict the invention to this specific type of assay.

Figure 1:
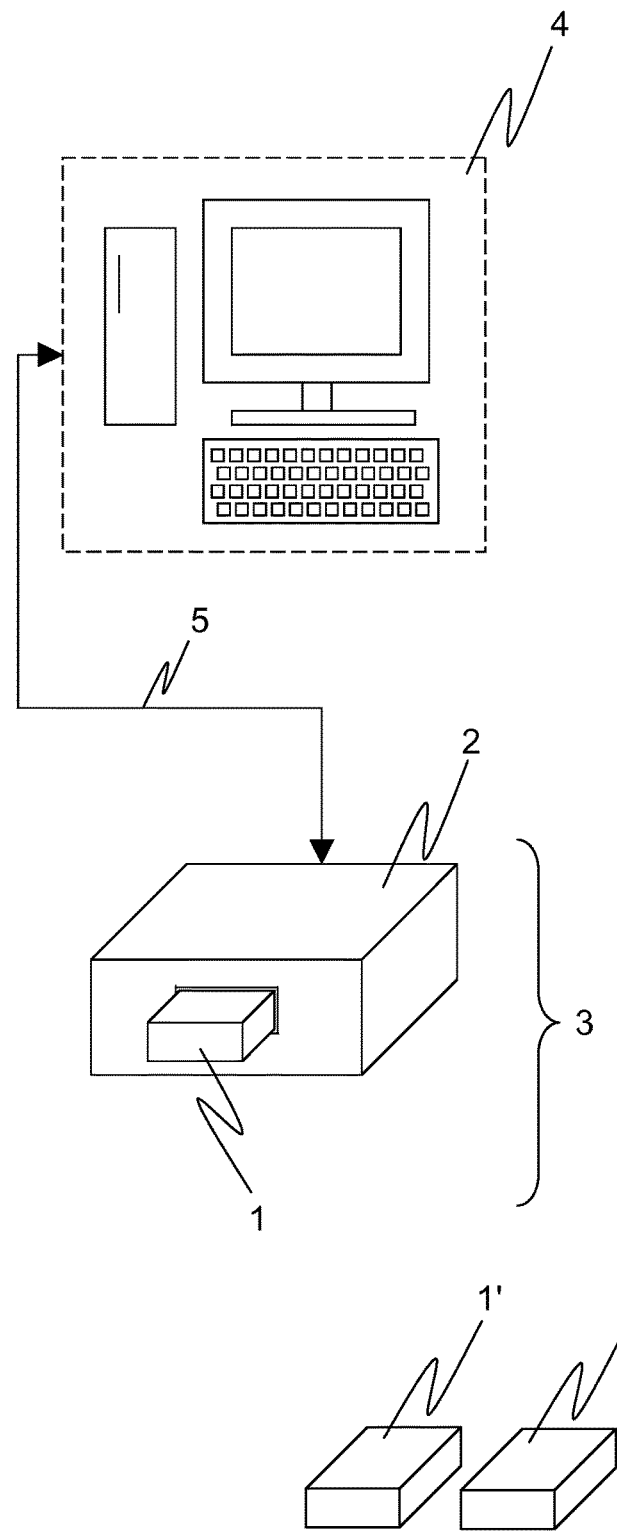
FIG. 1 schematically shows a diagnostic device according to the invention, connected with a computer system.

An exemplary embodiment of a diagnostic device 3 according to the invention is schematically shown in FIG. 1. The diagnostic device 3 comprises an assay unit 1 according to the invention in the form of a disposable microfluidic chip 1, on which the fluorescence assay test is carried out, and a reusable reader unit 2, with which the results of the fluorescence assay of the diagnostic tests can be read out from the assay unit 1. Two additional disposable assay units 1' are ready for later use.

The shown exemplary embodiment of a reader unit 2 comprises a slot on a side wall of the casing, in which an assay unit can be releasably mounted. In the figure, an assay unit 1 is shown inserted in the slot. However, a skilled person will know other possibilities how reader unit and assay unit can be operationally coupled in a releasable manner.

The reader unit 2 is connected via a generic data link 5 (e.g. a USB connection or a WLAN connection) with a generic computer system 4. The computer system 4 shown in the given example is a standard computer device, namely a desktop computer with display and keyboard. However, the computer system may also be a portable computer device, for example a mobile computer, a tablet device, a smartphone, or the like.

The disposable assay unit 1 comprises the one-time use fluorescence assay elements, and advantageously all other parts that come into contact with sample material, and thus are contaminated after use. The reusable reader unit 2 advantageously comprises all parts that can be used more than once, particularly the expensive optical and electronic parts of the excitation and detection systems, as well as electronic parts needed for detection, evaluation, and device control.

Depending on the specific embodiment of the invention, the computer system 4 may be used to obtain measurement data from the reader unit and to evaluate said data, and/or to present the evaluated data as diagnostic results to a user, and/or to send operational instructions to the reader unit, etc. However, it is also possible to integrate part or all of such functions in the reader device, which in the later case then could be used as a stand-alone diagnostic device.

A disposable assay unit 1 according to the invention is advantageously realized as a microfluidic chip, comprising as its two main functional components a microfluidic system 20, and a photonic system 60.

Figure 2:
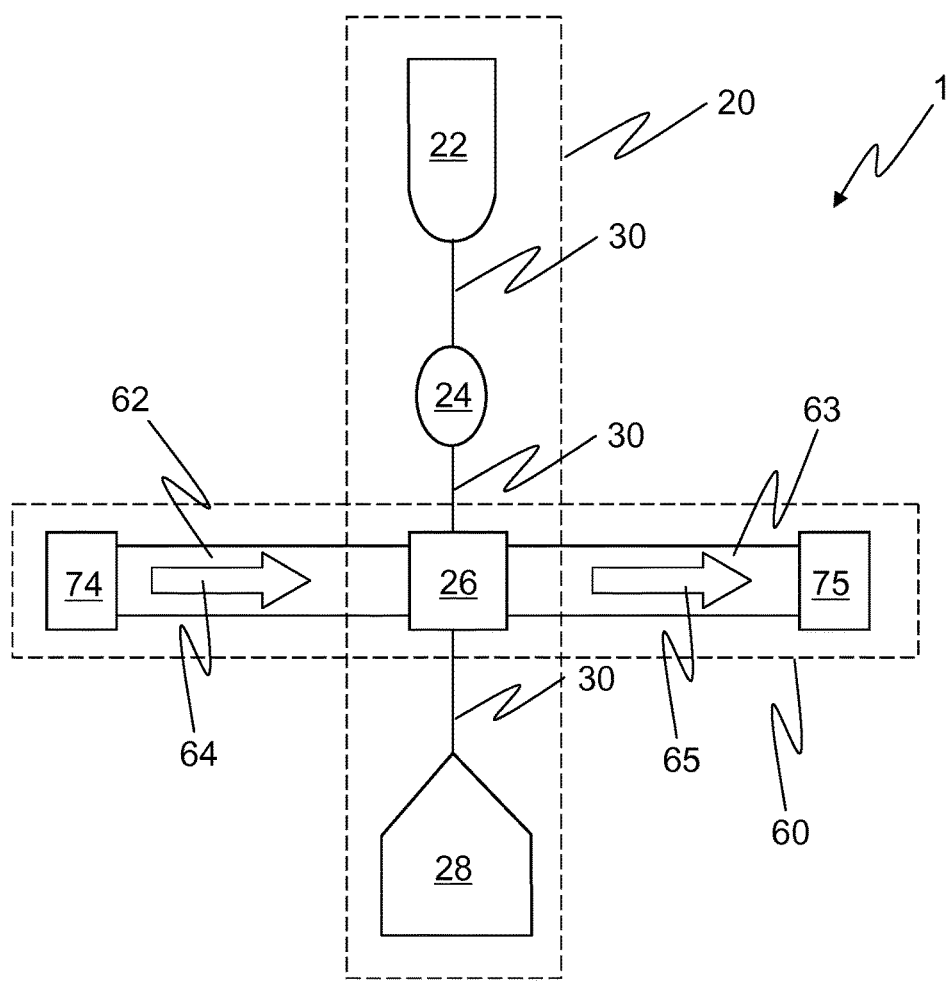
FIG. 2 schematically shows an embodiment of an assay unit according to the invention, with a microfluidic system and a photonic system.

An advantageous embodiment of an assay unit 1 according to the invention is schematically depicted in FIG. 2, showing a functional schematic of the microfluidic system 20, and the photonic system 80.

The microfluidic system 20 comprises in the downstream direction an injection pad 22, a sample preparation section 24, a detection site 26, and a capillary pump 28. The different sections are fluidly connected by a narrow fluidic channel 30, through which the analyte solution proceeds accordingly during the diagnostic test procedure. In the injection pad 22, the fluid sample on which the diagnostic test is to be carried out is introduced into the system. In the sample preparation section 24, the sample is prepared for subsequent analysis. The sample preparation section can include features such as a filter, a lysis, and an incubation chamber, depending the kind of sample and analytical test to be performed. In an incubation chamber, the necessary preparatory chemical reactions take place, for example the coupling reaction of the analyte molecules with the fluorescence markers. In the detection site 26, the analyte solution interacts with the immobilized capture antibodies, and the resulting fluorescence signal is measured. The capillary pump 28 conveys the sample fluid, or analyte solution respectively, along the fluid path according to the diagnostic test protocol.

The photonic system 60 of the assay unit comprises one or more coupling elements 74, with which an excitation light beam 64 is coupled into one or more in-going waveguides 62. Said waveguides 62 direct the excitation light 64 toward the detection site 26, where the evanescent tail of the excitation light excites the fluorescence markers near the waveguide surface, and the emitted fluorescence light is detected. This will be explained in more detail further below.

The waveguides of the photonic system cross the detection site 26 in an essentially perpendicular angle, and then the out-going waveguides 63 direct the remaining light away to other coupling elements 75, where the light is coupled out of the photonic system.

Figure 3:
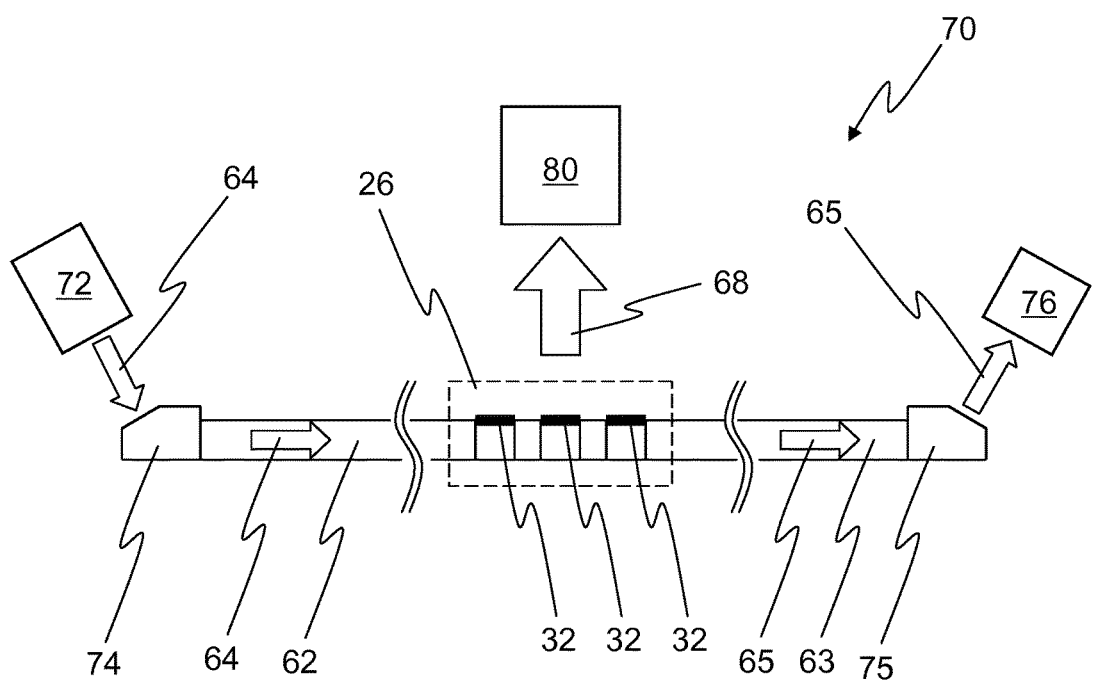
FIG. 3 schematically shows a side-view of an optical system of a diagnostic device according to the invention, including the photonic system of an assay unit according to the invention.

In FIG. 3, the optical system 70 of a diagnostic device 3 according to the invention is shown in a schematic sideview. The optical system on one hand includes the photonic system 60 of the disposable assay unit 1, as well as the optical elements that are advantageously realized as part of the reader unit 2, and can be reused.

The optical system 70 comprises an excitation light source 72. The light source can be realized for example as a laser diode, a light emitting diode (LED), a super luminescent diode, or the like, and generates the excitation light 64 necessary for exciting the fluorophores.

The use of laser diodes has two main advantages, particularly if the laser diode is both laterally and longitudinally monomode. The resulting very narrow line width makes the separation of the spectral regions of excitation and emission easier than in the case of sources having a larger line width. Second, lasers benefit from large optical étendues, which make them ideally suited to efficiently couple light into a waveguide.

Instead of one single light source, serving all waveguides, a multitude of light sources, such as for example a diode array or the like, can be used. The light source 70 is advantageously realized as a part of the reusable reader device 2 of a diagnostic device 3 according to the invention. However, it may also be realized as part of the disposable assay unit 1.

The optical system furthermore comprises a coupling element 74 that is apt to couple the beam of excitation light 64 emitted by the light source 72 into the planar waveguide 62, guiding the light toward the detection site 26. The coupling element 74 can be either included on the disposable assay unit/microfluidic chip 1, as a part of the photonic system 60, or can be provided as an external element that is included in the reusable reader device 2.

The coupling element 74 can for example be realized as a lens that focuses the excitation beam 64 onto a waveguide input facet, or as a prism to evanescently couple the light beam 64 into the waveguide 62, as shown in the figure, or as a vertical coupler such as a grating coupler or a micromirror. A lens that couples light into a waveguide through its facet has the advantage of being very efficient assuming there is a good mode matching between the laser mode and the waveguide mode. This configuration is nevertheless sensitive to alignment mismatches. Prism couplers are mechanically stable but require the prism to be placed at very short distances (typically of the order of 100 nm or less) from the core of the waveguide to be efficient. Grating couplers have the advantage of not requiring any external element such as a lens or a prism since the grating is fabricated directly onto or in the vicinity of the core of the waveguide. Although their dimensions are small, they can be used in conjunction with an adiabatic taper in order to loosen the mechanical tolerances on the light source alignment (c.f. D. Taillaert et al., "*An Out-of-Plane Grating Coupler for Efficient Butt-Coupling Between Compact Planar Waveguides and Single-Mode Fibers*", IEEE J. Quantum Electronics, Vol. 38, No. 7, July 2002).

In an alternative variant, the optical system 70 includes one or more Y-junctions or splitters (not shown), in order to accurately distribute the excitation light coupled into one single waveguide into a set of subsequent distribution waveguides. Each of these distribution waveguides carries the excitation light from the in-coupling site to the detection site.

The detection site 26 consists of a photonic structure such as a waveguide, or a cavity. Waveguides are very advantageous structures for fluorescence excitation because they can confine large amounts of optical power in the direction that is transverse to the propagation direction, in dimensions of the order of a few micrometers or less, and over distances that can reach several millimetres. The evanescent tail at the interface of a strongly confining waveguide can be absorbed by neighbouring molecules such as fluorophores and reemit fluorescent emission that is then detected.

Optical micro- or nanocavities can confine light temporally. Using them in combination with a waveguide provides an additional advantage over waveguides alone. A given amount of electromagnetic energy in resonance with the cavity mode will remain stored within the cavity for a certain amount of time. This amount of time is given by its quality factor (Q). The larger the quality factor of a cavity, the longer it takes for the energy within the cavity to decay. This phenomenon can be advantageously used for fluorescence excitation since light stored in the cavity can interact for a longer time with an absorbing molecule (like a fluorophore) in its vicinity than a standard propagating wave. This directly results in a large increase of the fluorescence signal, for a given waveguide input power.

There are two main types of optical micro- or nanocavities. The first type corresponds to the whispering gallery mode (WGM) resonators, which include microrings, microtoroïds and microspheres. The second type corresponds to mirror and photonic bandgap (PBG) resonators, and includes Fabry-Perot (FP) cavities, Distributed Bragg Resonators (DBR) and Photonic Crystal (PhC) cavities, each of which can be implemented in a variety of configurations.

Within the detection site one or more assay spots 32 are provided, where capture antibodies for a specific analyte protein are immobilized on the surface of the waveguide structure, and come into contact with the analyte solution. In the case of a positive response to the immunoassay, the target antigen/analyte protein, which has been fluorescently labelled in the upstream incubation chamber 24, are captured by the immobilized antibodies near the surface of the waveguide structure, resulting in an aggregate of fluorophores on the surface. The evanescent tail of the confined electromagnetic field of the excitation light within the waveguide structure excites the aggregated fluorescent markers, which subsequently emit fluorescence light 68.

The fluorescence emission 68 of the fluorescence markers is detected by a detector unit 80, arranged above the matrix of assay areas 32. In a possible embodiment the detector unit 80 can be realized as a CCD camera system. Such an embodiment allows the parallel detection of the fluorescence emission signal of a multitude of assay areas 32. The detector unit 80 is advantageously realized as part of the reusable reader unit 2.

Alternatively, or in addition, a detection unit can also be provided on the side of the waveguide structure opposite to the assay areas 32.

Depending on the specific design of the optical system, further optical elements may be provided, in order to optimise the sensitivity of the detector. For example can a band-filter be applied for removing excitation stray-light prior to detection.

The remaining portion 65 of the excitation light is guided away from the detection site through another waveguide 63. The waste excitation light is then coupled out of the waveguide 63 and photonic system 60 through another coupling element 75, similar to the first coupling element 74. The light amplitude can then be detected with an appropriate detection element 76, such as for example a focussing lens land a photodiode. The obtained signal could be used as a reference, for taking into account, for example, specific attenuation values of an individual disposable assay unit 1, 1', in order to increase sensitivity and accuracy.

In another approach the remaining light beam 65 is absorbed, in order to avoid reflection of the waste excitation light back into the photonic system 60, where unwanted background noise in the detection site due to scattering or the like could be the result.

Figure 4:
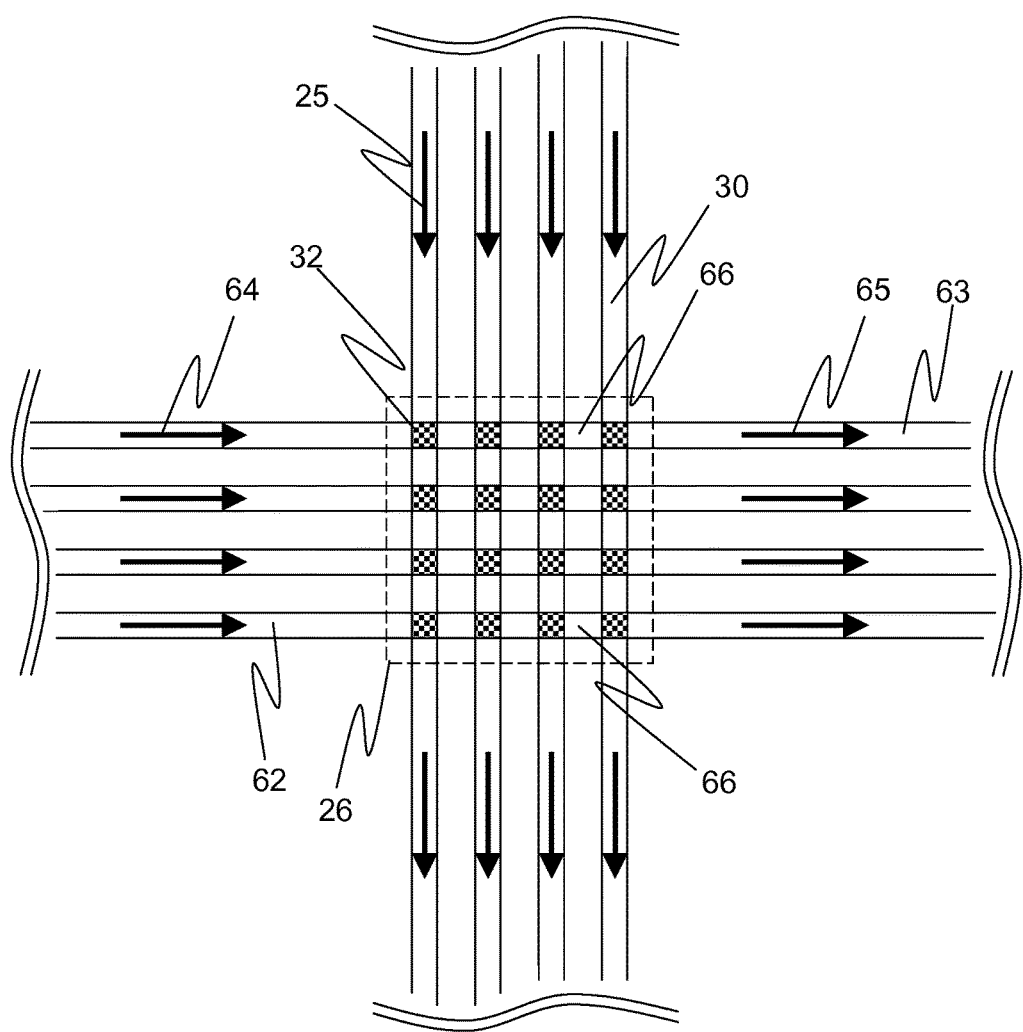
FIG. 4 schematically shows a top-view of an assay unit according to the invention, with a matrix of capture spots at the crossing points of a multitude of waveguides and microfluidic channels.

A top-view onto the detection site 26 of an assay unit 1 according to the invention is schematically shown in FIG. 4. On the left, four identical waveguides 62 direct the excitation light 64 from a, in-coupling structure (not shown) toward the detection site 26 in the centre. After having passed the detection site, the out-going waveguides 63 lead the remaining light 65 away, toward an out-coupling structure on the right (not shown).

In the detection site 26, the waveguides cross four microfluidic channels 30 that convey analyte solution 25 from an upstream incubation chamber (not shown) through the detection site 26 toward a downstream dump site or the like. At the assay areas 32, the places where the microfluidic channels 30 cross the waveguide structure 66, the fluorophore-marked analyte solution comes into contact with the immobilized capture antibodies on the surface of the waveguide structure. In case the fluorescence-labelled antigen corresponding to the specific antibody of a certain assay area 32 is present in the analyte solution, the analyte-fluorophore complex will aggregate on the surface, where it can be excited by the evanescent tail of the excitation light wave in the waveguide structure. Possible embodiments of such waveguide structures will be explained further below.

Depending on the concept, it is principally possible to provide each of the N different assay areas with an immobilized capture antibody for a different target protein, which allows the parallel, multiplexed immunoassay detection of N proteins. Alternatively redundant tests and controls may be provided, for less than N proteins, but with further increased reliability.

A possible advantageous geometry of a waveguide structure 66 at the detection site is schematically depicted in FIG. 5. The waveguide structure comprises of a substrate layer 102, a core layer 104 of higher refractive index than the substrate 102, and a cladding layer 106 of lower refractive index than the core layer 104. The upper surface 105 of the core layer is in direct contact with the test medium 110, typically a physiological solution such as plasma. Said upper surface provided with immobilized capture antibodies 112, as shown in FIG. 5(a), which form a capture spot 27. The capture antibodies 112 bind specifically to certain antigens, namely the protein molecules 114 that should be detected. As a result the capture spot 27 is selectively sensitive only for such proteins.

In the presence of said certain antigen 114 in the medium 110, antigen-antibody complexes 117 form on the surface 105. The antigens 114 that have previously formed complexes 118 with the abundantly present fluorescence markers 116 bind to the immobilized capture antibodies 112 on the surface of the core layer 105, as shown in FIG. 5(b).

The schematic curve on the right of FIG. 5(b) symbolizes the electric field distribution for the first guided mode of the excitation light along the axis perpendicular to the surface. While most of the field is located within the waveguide core 104, two evanescent tails are present outside the waveguide core, one on each side of the core. Due to the imbalance in the refractive index profile between the substrate layer 102 and the test medium 110, the larger evanescent tail will be located in the substrate, while the smaller evanescent tail is located in the test medium 110. Thus the excitation light is essentially only present within the analyte solution 110 in close vicinity to the core layer surface, and only fluorophores 116 close to the surface can absorb an excitation light photon, and subsequently emit a fluorescence photon. Unreacted fluorescence markers 116 within the analyte solution are not excited, and which decreases signal background and increases signal-to-noise ratio.

It should be mentioned that the dimensions in FIG. 5(b) are purely schematic. The antibodies have a size of approx. 10 nm, and the waveguide and electric field have dimensions in the range of a few micrometers.

It is not detrimental if also neighbouring areas of the core surface 105 are provided with capture antibodies. It may be simpler for manufacturing not to distinguish between waveguide core surface and neighbouring cladding layer surface when producing the capture antibody coating. Fluorophores attached to antibodies on the cladding layer will simply not be excited, due to the lack of excitation field.

Figure 6:
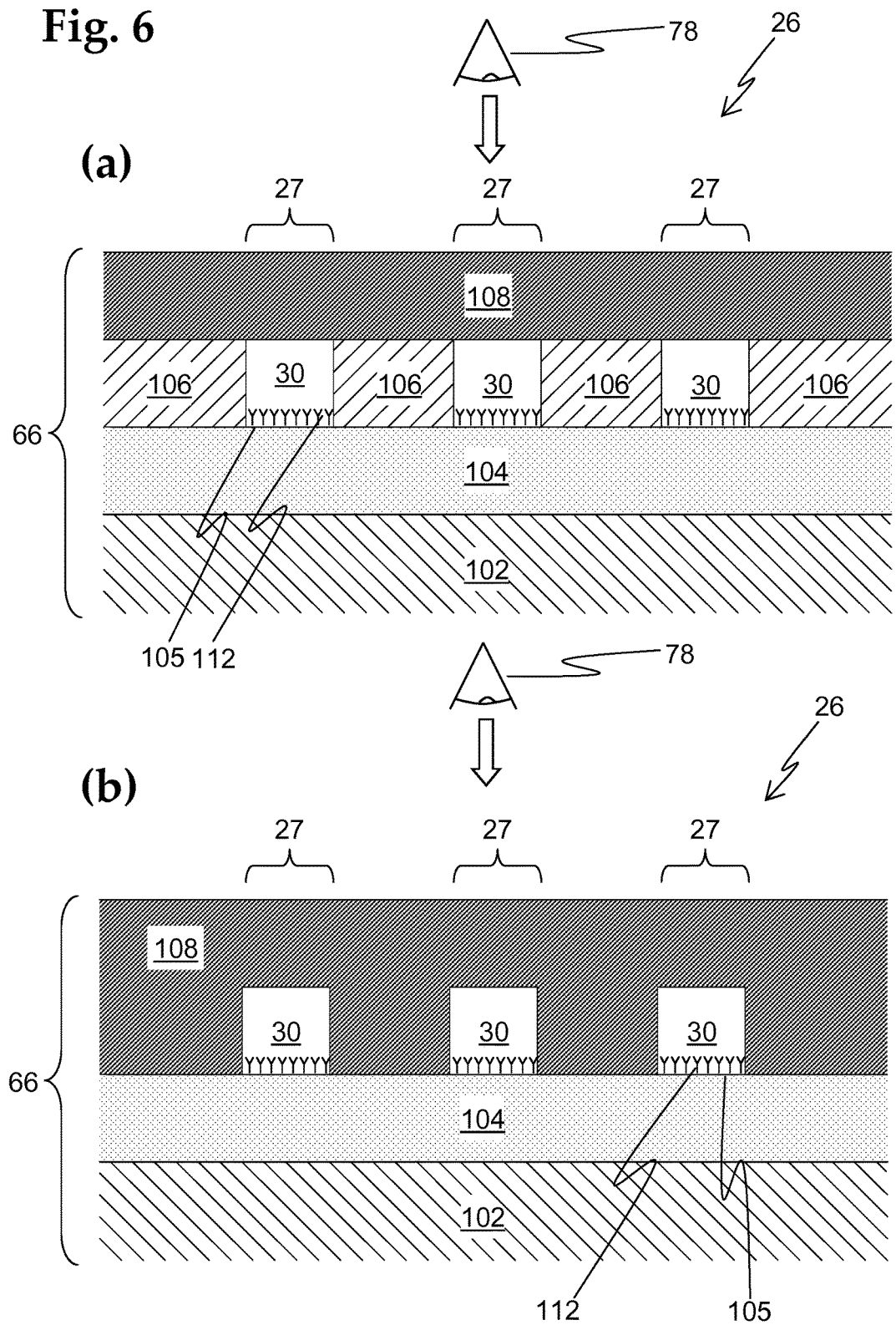
FIG. 6 schematically shows a cross-section through two variants of a possible geometry of a waveguide structure at a detection site, along the axis of a waveguide structure.

FIG. 6(*a*) schematically shows a possible configuration of the waveguide 66 structure and microfluidic channel 30 structure on a detection site 26 of a diagnostic device 1 according to the invention, in a cross-sectional view along the axis of the waveguide core 104. Both the photonic and microfluidic structures are implemented on the substrate layer 102 of the chip. The core layer 104 is embedded in a surrounding cladding layer (not visible), similar to the example in FIG. 5. The microfluidic channels 30 are located in the cladding layer 106, which extends above the core layer 104. A superstrate layer 108 is deposited on top of the cladding layer 106, and forms the cover of the microfluidic channels 30.

At the capture spots 27, the microfluidic channels 30 cross the one or more waveguide cores 104. At this sites, the surface 105 of the waveguide core 104 lies open, and is provided with capture antibodies 112. Since the fluorescence emission of fluorophores on the detections spots has to be optically detected, the superstrate layer 108 and/or the substrate layer 102 are chosen to be transparent in the visible range.

In a second possible configuration, as it is shown in FIG. 6(*b*), the photonic structures are implemented on the substrate 102, the waveguide core 104 being embedded in the cladding layer (not visible), similar to the example in FIG. 5. The microfluidic structures 30 on the other hand are in the superstrate layer 108.

For fabricating the complex structures as shown above, layers of different materials can be deposited on the substrate 102. Alternatively, two elements can be produced separately and finally superposed on top of each other, to form the complete chip structure. For example, it is possible to manufacture a structure as depicted in FIG. 6(*b*) by deposing cladding layer and embedded waveguide core 104 on the substrate, by producing a superstrate cover 108 with micro channels 30, and mounting the cover 108 on the substrate part.

Figure 7:
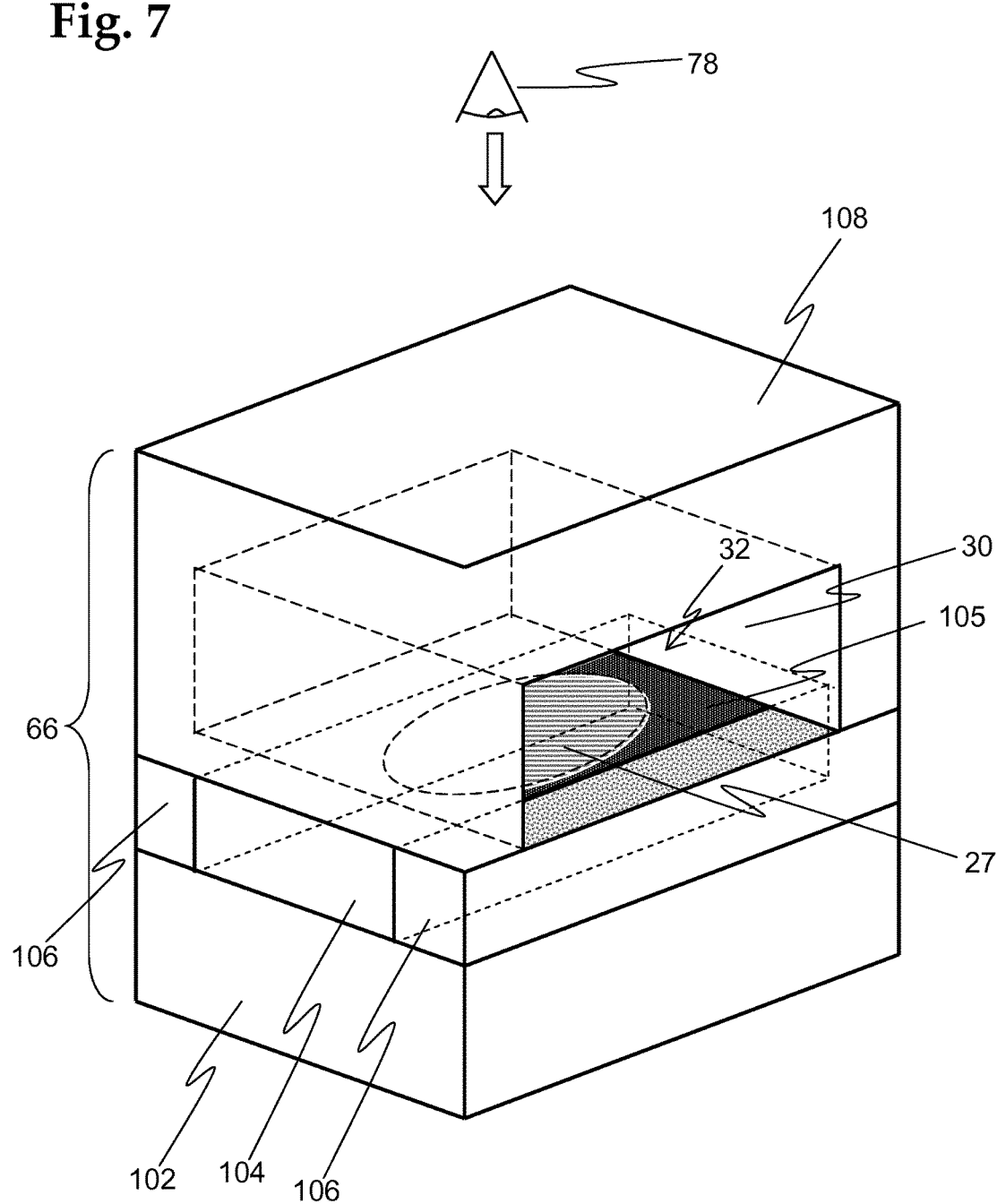
FIG. 7 shows a perspective view of the waveguide structure and microfluidic structure at a capture spot.

To further explain the structure of the crossing waveguide structure 66 and microfluidic channel 30 at an assay area 32, FIG. 7 shows a cut-out detail of a structure similar to FIG. 6(*b*) in a perspective view. On a chip substrate layer 102 a waveguide core 104 is deposited, embedded in a cladding layer 106. On top of the cladding/core layer 106/104, a superstrate layer 108 is deposited, in which a microfluidic channel 30 is located. At the place where the channel 30 crosses the waveguide core 104, the surface 105 of the core lies open (dark grey area), as well as the surface of the neighbouring cladding layer (light grey area). At least a part of the open core surface 105 is provided with a layer of immobilized capture antibodies (not shown), forming a capture spot 27, on which later the fluorophore marked analyte proteins can attach.

During operation, the microfluidic channel is filled with the analyte solution, which thus covers the surface of core layer 104 and cladding layer. Excitation light is guided in the core layer 104. The evanescent tail of the excitation light field overlaps with the area in close vicinity of the core surface 105. Fluorophores present in that area are excited, and emit fluorescence radiation. Part of the fluorescence radiation passes through the transparent superstrate layer 108, and can be observed 78 on the outside.

An alternative geometry of a waveguide structure 66 at the capture spot 27 is schematically shown in FIG. 8. In this example, no embedding cladding layer is used. As a result the core layer 104 is protruding from the substrate layer 102. Both the lateral surfaces 105' and the upper surface 105 of the core layer are in contact with the test solution 110. Capture antibodies 112 are immobilized on all accessible surfaces of the core layer, which increases the total interaction area, and thus the available fluorescence signal and signal-to-noise ratio.

For an embedded waveguide core geometry of as shown in FIGS. 5 to 7, in the assay area 32 the waveguide core 104 changes directly from a section where its upper surface is covered by a superstrate layer 108 or cladding layer 106 to a section where it is in contact with the analyte solution.

In a protruding waveguide core geometry as shown in FIG. 8, it is advantageous to provide an adiabatic change from the embedded geometry, where the core is embedded in substrate layer, cladding layer and superstrate layer, to the protruding geometry at the capture spot, where three surfaces of the core lie open and are in contact with the analyte solution.

A possible embodiment of such an advantageous geometry is shown in FIG. 9. A waveguide core 104 is deposited on the substrate 102, embedded on both lateral sides by a cladding layer 106. The waveguide structure is covered by a transparent superstrate layer 108, in which the microfluidic channels 30 are formed. The microfluidic channels and the waveguides 62 cross at a perpendicular angle. In the assay area 32, when the waveguide layer 104 leaves the side wall 31 on the left of the microfluidic channel 30, the core 104 is initially laterally embedded in the cladding layer 106. The cladding layer then decreases in height, forming a taper-like structure until in a central portion 107 both the upper surface 105 and the two lateral surfaces 105' of the waveguide core 104 lie open. On the right side, the cladding layer increases again in height, forming a taper-like structure, until waveguide core 104 and cladding layer 106 reach the sidewall 31' on the right. This gradual change between the fully embedded situation and the exposed situation reduces detrimental optical effects, such as reflections, loss of guided excitation light etc.

Similar to FIG. 8, the surfaces 105, 105' of the waveguide core are provided with immobilized capture antibodies (not shown), for capturing the complex of the analyte protein and the fluorophore.

As previously explained, in an assay area 32 only a fraction of the guided excitation field overlaps with the test medium, in the close vicinity of the interface of the waveguide. In addition to the amount of contact area, which defines the actual amount of detectable fluorophores, also the size and distribution of the capture spots 27 are an important factor to generate an adequate fluorescence signal.

Figure 10:
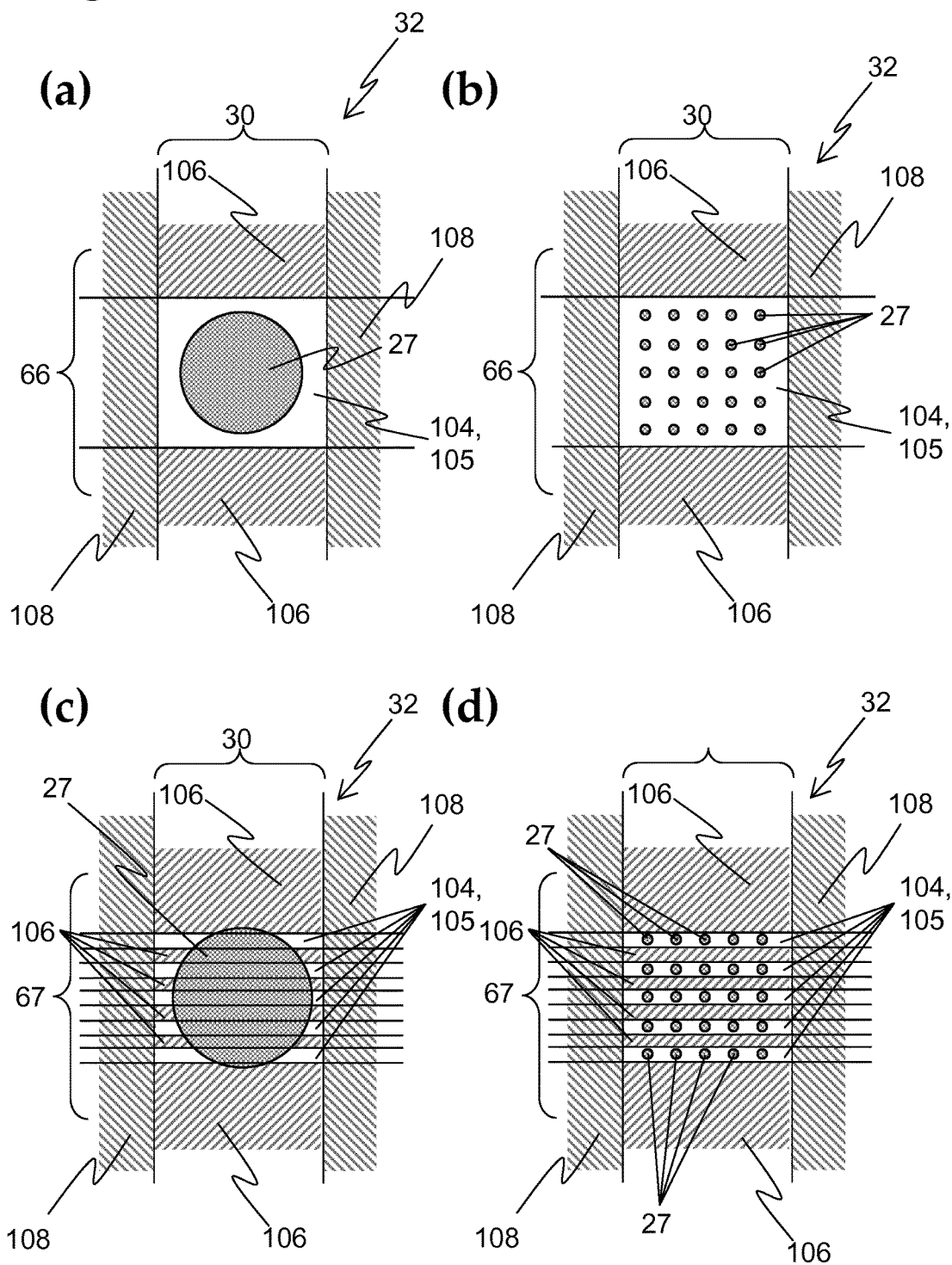
FIG. 10 schematically shows four advantageous geometries of waveguide structure and microfluidic channel at a capture spot.

Four different approaches for realizing a capture spot for a distinct protein molecule in an assay unit according to the invention are shown in FIG. 10, having different ratios between the size of the protein spots and the width of the waveguide.

FIG. 10(*a*), shows a top view of a possible embodiment of a waveguide structure 66 and capture spot 27, similar to FIG. 7, with removed cover superstrate layer. A single laterally multimode waveguide 66 comprises a waveguide core 104 embedded in a cladding layer 106. The waveguide core 104 is comparably wide (e.g. 50 micrometer width of core 104) in relation to the excitation wavelength in the visible or near UV range. At the crossing point of waveguide 66 and microfluidic channel 30, a single, large capture spot 27 is present. The capture spot is comparable in size with the waveguide width, and comprises a coating of immobilized capture antibodies, provided on top of the surface 105 of the waveguide core 104. Excitation light in the multimode waveguide 66 excites fluorophores present at the surface 105 of the waveguide core.

In an alternative embodiment as shown in FIG. 10(*b*), a matrix of smaller capture spots 27, with a width of e.g. 5 micrometer, is arranged on the surface 105 of the waveguide core. The multimode waveguide 66 has similar dimensions as in the previous embodiment of FIG. 10(*a*). All the capture spots 27 are sensitive for the same analyte protein. The result is a matrix of small fluorescence emission dots, instead of a large fluorescence emission spot.

In another alternative embodiment as shown in FIG. 10(*c*), a bundle of five single mode waveguides 66 crosses the microfluidic channel 30. The waveguide cores have a width of a few micrometer. A large capture spot 27, similar to FIG. 10(*a*), is present on the surfaces 105 of the waveguide cores and the neighbouring areas of the cladding layer 106 surface. Only fluorophores on the surface of the waveguide core will be excited.

In yet a further embodiment, as it is depicted in FIG. 10(*d*), five single mode waveguides 66 similar to FIG. 10(*c*) cross the microfluidic channel 30. A matrix of smaller capture spots 27 similar to FIG. 10(*b*) is arranged on the surfaces 105 of the waveguide cores. The waveguide 66 has similar dimensions as in the previous embodiment of FIG. 10(*a*). All the capture spots 27 are sensitive for the same analyte protein. The result is a matrix of small fluorescence emission dots, instead of a large fluorescence emission spot.

Advantageously, the integration of the overall fluorescence emission of a certain assay area 32 is carried out when the image of the detection site 27 is evaluated. For that purpose it is not necessary for a detection unit to resolve the distinct capture spots 27 of an assay area 32.

Figure 11:
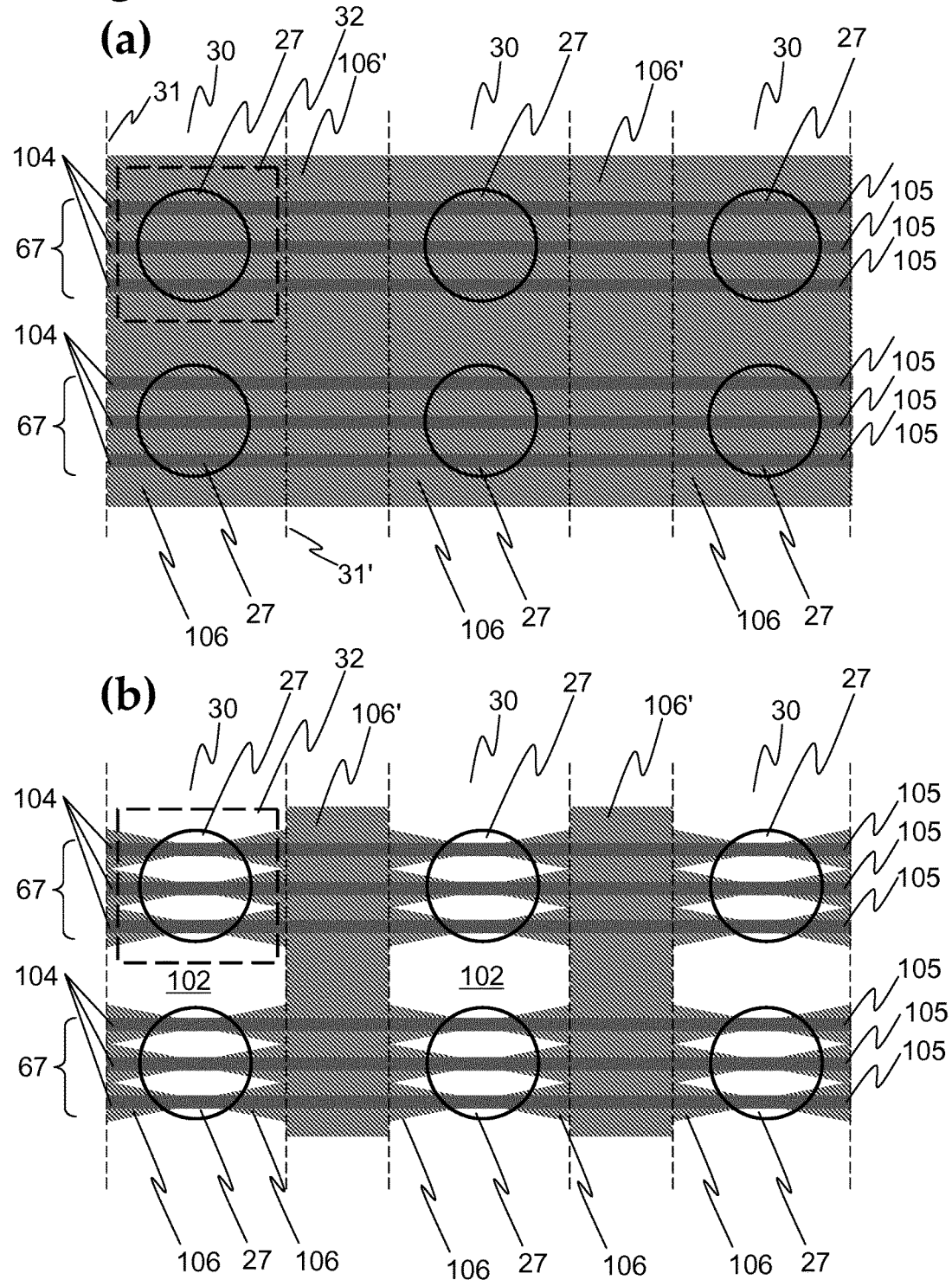
FIG. 11 shows a schematic view of a detail of a detection matrix of a detection site, (a) with an embedded waveguide structure, and (b) with a protruding waveguide structure.

A detail of a subset of assay areas 32 of a detection site 26 of an advantageous embodiment of an assay unit according to the invention is schematically shown in FIG. 11(*a*), the geometry of the waveguide structure being analogue to FIG. 10(*c*). The view is similar to the view of a detection system arranged above the superstrate layer (not shown). In the shown detail, two waveguide bundles 67 of three monomode waveguides cross three microfluidic channels 30. The waveguide cores 104 are embedded in the cladding layer 106. At the crossing area 32 of waveguide bundles 67 and microfluidic channels, large capture spots 27 are arranged.

Each capture spot 27 is sensitive for a different analyte protein. Thus an evaluation system analysing a digital picture of the fluorescence emission at the detection site, obtained by detector unit, will be able to determine the presence of a certain analyte at a certain capture spot by measuring and integrating the overall signal in the area of a capture spot 27. The distance between the different columns and rows of capture spots is chosen taking into account different parameters. The minimum distance is chosen particularly in regard to the resolution limit of the detection system, which has to be able to clearly distinguish the signal of different assay areas 32, as well as possible cross-talk in the photonic system between neighbouring assay areas.

A variant of the embodiment discussed above with a protruding waveguide structure is shown in FIG. 11(*b*), using transition between embedded core and protruding core similar to FIG. 9. The saw-tooth structures around each waveguide core in the microfluidic channels thus correspond to tapers of cladding material, used to adiabatically transform the waveguide mode from the embedded configuration to the protruding configuration. Cladding boundaries 106' prevent cross talk between adjacent microfluidic channels 30.

Figure 12:
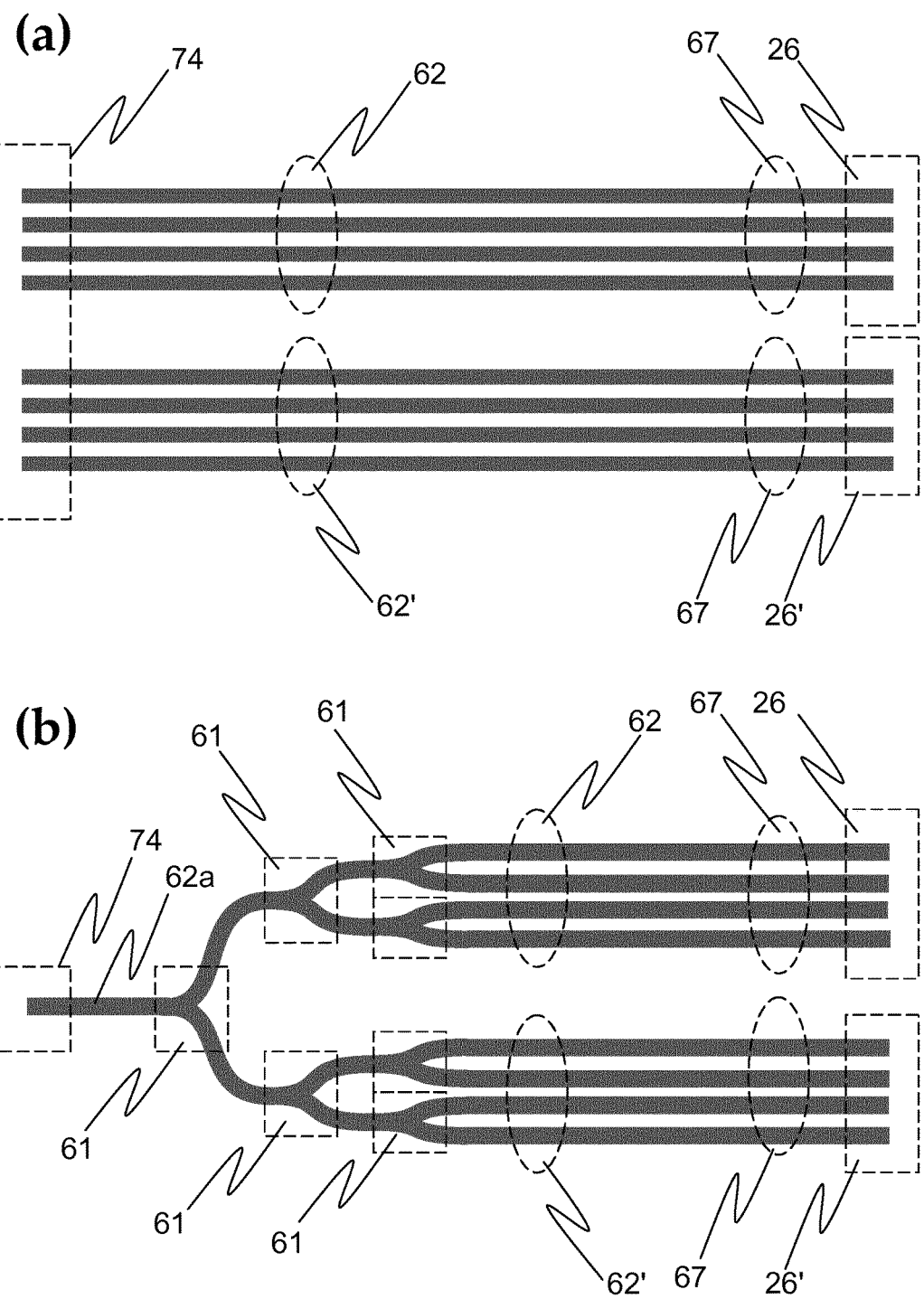
FIG. 12 is a schematic view of two advantageous excitation light intensity distribution architectures for the array of waveguides in an assay unit according to the invention.

Good uniformity of the excitation light power coupled into each of the waveguides is an important aspect of the matrix immunoassay test as carried out on an assay unit according to the invention, in order to obtain comparable relations between the fluorescence signals of the different capture spots. FIG. 12 provides an illustration of two advantageous light distribution schemes.

In a first approach as given in FIG. 12(*a*), with two bundles 66 having four waveguides each, each waveguide is completely independent from each other, from the in-coupling site 74 on the left to the detection sites 26, 26' on the right, and finally to the out-coupling site (not shown). Excitation light is injected in each of the waveguides separately, and the elements to provide each waveguide with similar excitation intensity are located outside of the microfluidic chip, advantageously on the reusable reader unit. Uniform light intensities across the different waveguides can be achieved for example by a linear illumination device, with a moving mirror that distributes the light of a common excitation light source onto the coupling elements of the different waveguides.

In a second approach as given in FIG. 12(*b*), a common input waveguide 62*a* is successively divided into subsequent waveguides 62, 62' by the means of Y junctions/waveguide splitters 61. In this manner uniform excitation power is provided to each of the detection sites. The means for equally distributing the excitation light are located on the disposable assay unit.

FIG. 13 illustrates two configurations to couple light from a waveguide core (104) into an optical cavity (90). The electromagnetic field coupled into the optical cavity 90 is temporarily stored within the cavity, and is used to evanescently excite the neighbouring fluorophores on the capture spot (27).

In one advantageous embodiment as depicted in FIG. 13(*a*), an optical cavity (90) is located on the side of the waveguide core (104) such that the evanescent tail of the propagating mode can excite the resonant mode of the cavity. The resonant mode possesses itself evanescent components, which can be absorbed by the fluorophores in the capture spot (27). The excited fluorophores emit fluorescent light when returning to their ground state. The wavelength of the excitation light to be transmitted through the waveguide has to lie within the waveguide bandwidth, and has to be tuned to the resonance wavelength of the cavity, so that the electromagnetic energy couples to the cavity mode and is free to excite fluorophores in the vicinity.

In one variant of such an embodiment, the waveguide consists of a ridge waveguide and the cavity consists of a microring cavity that supports a whispering gallery mode. The advantage of this configuration is that it can be easily fabricated using standard lithography methods. Microring resonators can bear optical modes with very large quality factor, leading to strong light-matter interaction and thus enhanced excitation of the fluorophores. In another advantageous variant the waveguide consists of a photonic crystal W1 waveguide and the cavity can consist of a photonic crystal L3 cavity.

In another advantageous embodiment as depicted in FIG. 13(*b*), the optical cavity (90) is positioned in between two aligned waveguide cores (104, 104'). In this configuration, the light guided in the input waveguide (62, 104) couples to the cavity (90) and the second, outgoing waveguide (63, 104') as long as the excitation wavelength is tuned to the resonance wavelength of the cavity.

Various references are cited throughout the specification, the disclosures of which are each incorporated herein by reference in their entirety.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims.

The invention claimed is:

1. An assay unit for carrying-out fluorescence-detected assays on one or more physiological samples, comprising:
    a microfluidic chip with a microfluidic system to convey a physiological sample or analyte solution through one or more microfluidic channels arranged on the chip,
    a photonic system with two or more rectangular waveguide structures arranged on the chip and configured to guide excitation light,
    a plurality of detection sites within the one or more microfluidic channels, each of the detection sites at and within an intersection crossing point of the one or more microfluidic channels with one of the two or more rectangular waveguide structures, the detection sites each comprising a capture spot on a surface of a corresponding one of the two or more rectangular waveguide structures, the capture spot including a coating of capture molecules of an assay, immobilized directly on the surface of the corresponding one of the two or more rectangular waveguide structures,
    wherein the two or more rectangular waveguide structures are configured to guide an evanescent field of light to overlap with and pass through the detection sites and excite fluorophores present in the microfluidic channel at the capture spots,
    wherein each of the two or more rectangular waveguide structures comprises a linear structure with a certain refractive index that is surrounded by media of a lower refractive index, such that light within the two or more rectangular waveguide structures can freely propagate along a linear dimension of the linear structure, but is confined in lateral dimensions outside of the detection sites, and
    wherein each of the detection sites is not covered by the media of the lower refractive index, whereby the evanescent field of light is not confined in a lateral dimension through the detection sights.

2. An assay unit according to claim 1, wherein in the detection sites, a core of the two or more rectangular waveguide structures is arranged on a substrate layer, and is embedded in a cladding layer, such that only an upper surface of the core of each waveguide structure opposite to the substrate layer faces the capture spot and the inner volume of the microfluidic channels.

3. An assay unit according to claim 1, comprising one or more coupling elements for coupling a light beam into the two or more rectangular waveguide structures, and/or one or more coupling elements for coupling a light beam out of the two or more rectangular waveguide structures.

4. An assay unit according to claim 1, further comprising a superstrate layer on top of a substrate cladding layer, and forming a cover of the microfluidic channels.

5. An assay unit according to claim 1, wherein excited fluorophores emit fluorescence light from the detection sites.

6. An assay unit according to claim 5, wherein the evanescent field of light within the two or more rectangular waveguide structures can freely propagate through the detection sites, the fluorescence light is emitted above the detection sites, and the fluorescence light is detectable through the microfluidic channels.

7. An assay unit according to claim 6, further comprising a fluorescence detector unit above the detection sites and the microfluidic channels.

8. An assay unit according to claim 1, wherein a first portion of the light within the two or more rectangular waveguide structures propagates through the detection sites and a remaining portion of the light within the two or more rectangular waveguide structures propagates along the linear dimension of the linear structure away from the detection sites.

9. An assay unit according to claim 8, wherein the remaining portion of the light within the two or more rectangular waveguide structure is waste excitation light that is then emitted out of the two or more rectangular waveguide structures.

10. An assay unit according to claim 8, further comprising one or more coupling elements for coupling a light beam into the two or more rectangular waveguide structures, and/or one or more coupling elements for coupling the remaining portion of the light out of the two or more rectangular waveguide structures.

* * * * *